US006337193B1

(12) United States Patent
Tully et al.

(10) Patent No.: US 6,337,193 B1
(45) Date of Patent: Jan. 8, 2002

(54) EXPRESSION OF MANOSE-BINDING PROTEIN IN METHYLOTROPHIC YEAST

(75) Inventors: Raymond E. Tully, College Park, MD (US); G. Thomas Caltagirone, Reston, VA (US); Shawn S. Moyer, Lewisberry, PA (US); Michael T. Ronning, Simsbury, CT (US)

(73) Assignee: Aptagen, Inc., Herndon, VA (US)

( * ) Notice: Subject to any disclaimer, the term of this patent is extended or adjusted under 35 U.S.C. 154(b) by 0 days.

(21) Appl. No.: 09/198,603

(22) Filed: Nov. 24, 1998

(51) Int. Cl.$^7$ ............ C12P 21/02; C12N 1/15; C07H 21/04
(52) U.S. Cl. ............ 435/69.6; 435/69.1; 435/254.1; 435/254.11; 435/254.2; 435/254.21; 435/254.23; 536/23.1; 536/23.2; 536/23.4; 536/23.5; 536/23.7
(58) Field of Search ............... 536/23.1, 23.2, 536/23.4, 23.5, 23.7; 435/69.1, 69.6, 254.11, 254.2, 254.21, 254.23

(56) References Cited

U.S. PATENT DOCUMENTS 5,270,199 A * 12/1993 Ezekowitz ............... 435/372.1

OTHER PUBLICATIONS

Romanos et al., Yeast, vol. 8, pp. 423–488, 1992.*

Ikegawa et al, *Cytogenet Cell Genet.*, 71:182–186 (1995).

Pihlajaniemi et al, *The EMBO Journal*, 6(3):643–649 (1987).

Helaakoski et al, *Proc. Natl. Acad. Sci. USA*, 86:4392–4396(1989).

Freedman et al, *TIBS.*, 19:331–336 (1994).

LaMantia et al, *Cell*, 74:899–908 (1993).

Mizunaga et al, *J. Biochem.*, 108:846–851 (1990).

Lamberg et al, *The Journal of Biological Chemistry*, 271(20):11988–11995 (1996).

Vuorela et al, *EMBO J.*, 16(22):6702–6712 (1997) (Abstract).

* cited by examiner

*Primary Examiner*—David Guzo
(74) *Attorney, Agent, or Firm*—Sughrue Mion, PLLC

(57) ABSTRACT

Expression of Mannose-Binding Protein in methylotrophic yeast strains is disclosed.

16 Claims, 11 Drawing Sheets

FIGURE 1A

```
1    GGTAAATATGTGTTCATTAACTGAGATTAACCTTCCCTGAGTTTTCTCACACCAAGGTGAGGACCATGTCCCTGT
                                                                         MetSerLeuPhe

76   TTCCATCACTCCCTCTCCTTCTCCTGAGTATGGTGGCAGGCGTCTTACTCAGAAACTGTGACCTGTGAGGATGCCC
     ProSerLeuProLeuLeuLeuSerMetValAlaAlaSerTyrSerGluThrValThrCysGluAspAlaGln

151  AAAAGACCTGCCCTGCAGTGATTGCCTGTAGCTCTCCAGGCATCAACGGCTTCCCAGGCAAAGATGGGCGTGATG
     LysThrCysProAlaValIleAlaCysSerSerProGlyIleAsnGlyPheProGlyLysAspGlyArgAspGly

A <-- codon 54 mutation (in ATCC 67483)
226  GCACCAAGGAGAAAAGGGGAACCAGGCCAAGGCTTCAGAGGCCCCCTGAAAGTTGGGCCTC
     ThrLysGlyGluLysGlyGlyGluProGlyLeuGlnGlyLeuArgGlyLeuGlnGlyLeuProGlyLysGlyProPro 301  CAGGAAATCCAGGCCTGCCCTTCTGGGTCACCAGGACCCAAAAGGCCAAAAAGGAGACCCTGGAAAAAGTCCGGATGGTG
     GlyAsnProGlyProSerGlyProGlyProLysGlyProProGlyLysGlyAspProGlyLysSerProAspGlyAsp 376  ATAGTAGCCTGGCTGCCTCAGAAAGAAAGCTCTGCAAACAGAAATGGCACGTATCAAAAAGTGGCTGACCTTCT
     SerSerLeuAlaAlaSerGluArgLysAlaLeuGlnThrGluMetAlaArgIleLysLysTrpLeuThrPheSer 451  CTCTGGGCAAACAAGTTGGGAACAAGTTCTTCCTGACCAATGGTGAAATAATGACCTTTGAAAAAGTGAAGGCCT
     LeuGlyLysGlnValGlyAsnLysPhePheLeuThrAsnGlyGluIleMetThrPheGluLysValLysAlaLeu
```

FIGURE 1B

```
526  TGTGTGTCAAGTTCCAGGCCTCTCTGTGGCCACCCCAGGAATGTGCAGAGAATGGAGCCATTCAGAATCTCATCA
        CysValLysPheGlnAlaSerValAlaThrProArgAsnAlaAlaGluAsnGlyAlaIleGlnAsnLeuIleLys

601  AGGAGGAAGCCTTCCTGGGCATCACTGATGAGAAGACAGAAGGGCAGTTTGTGGATCTGACAGGAAATAGACTGA
        GluGluAlaPheLeuGlyIleThrAspGluLysThrGluGlyGlnPheValAspLeuThrGlyAsnArgLeuThr

676  CCTACACAAACTGGAACGAGGGTGAACCAAACAATGCTGGTTCTGATGAAGATTGTGTATTGTACTGAAAAATG
        TyrThrAsnTrpAsnGluGlyGluProAsnAsnAlaGlySerAspGluAspCysValLeuLeuLeuLysAsnGly

751  GCCAGTGGAATGACGTCCCCTGCTCCACCTCCCCATCTGGCCGTCTGAGTTCCCTATCTGAAGGGTCATATCAC
        GlnTrpAsnAspValProCysSerThrSerHisLeuAlaValCysGluPheProIleSTOP

826  TCAGGCCCTCCTTGTCTTTTTACTGCAACCCACAGGCCCACAGTATGCTTGAAAAGATAAATTATATCAATTTCC
```

FIGURE 2A

```
      EcoRI
  gcgcgaattCTGCTCCGTGTCCGACATGCTGCGCCGGCTCTGCTGCCGCTGTGCCTGCCGCCCTGGTGC
                   MetLeuArgArgAlaLeuLeuCysLeuAlaValAlaAlaLeuValArg GCGCCGACGCCCCGAGGAGGAGGACCACGTCTTGGTGCTGTGGGAAAAGCAACTTCGCGAGGCGCTGGCGCCC
  AlaAspAlaProGluGluAspHisValLeuValLeuTrpGluLysGlnLeuArgGluAlaLeuAlaAlaHis ACAAGTACCCGCCGGTGGAGTTCCATGCCCCCTGGTGTGCCACTGCAAGGCTCTGGCCCCTGAGTATGCCAAAG
  LysTyrProProValGluPheHisAlaProTrpCysGlyHisCysLysAlaLeuAlaProGluTyrAlaLysAla CCGCTGGGAAGCTGAAGGCAGAAGGTTCCGAGATCAGGTTGGCCAAGGTGGACGCCACGGAGGAGTCTGACCTAG
  AlaGlyLysLeuLysAlaGluGlySerGluIleArgLeuAlaLysValAspAlaThrGluGluSerAspLeuAla CCCAGCAGTACGGCGGCGTGCGCGGCTATCCCACCATCAAGTTCTTCAGGAATGGAGACACGCTTCCCCAAGGAAT
  GlnGlnTyrGlyGlyValArgGlyTyrProThrIleLysPhePheArgAsnGlyAspThrAlaSerProLysGluTyr ATACAGCTGGCAGAGAGGCTGATGACATCGTGAACTGGCTGAAGAAGCGCACGGGCCCGGCTGCCACCACCCTGC
  ThrAlaGlyArgGluAlaAspIleValAsnTrpLeuLysLysArgThrGlyProAlaAlaThrThrLeuPro CTGACGGCGCAGCTGCAGAGTCCTTGGTGGAGTCCAGCGAGGTGGCCGTCATCGGCTTCTTCAAGGACGTGGAGT
  AspGlyAlaAlaAlaAlaGluSerLeuValGluSerSerGluValAlaValIleGlyPhePheLysAspValGluSer CGGACTCTGCCAAGCAGTTTTGCAGGCAGCAGAGGCCATCGATGACATACCATTTGGATCACTTCCAACAGTG
  AspSerAlaLysGlnPheLeuGlnAlaAlaGluAlaAlaIleAspAspIleProPheGlyIleThrSerAsnSerAsp
```

|       |
|-------|
| 5     |
| 76    |
| 151   |
| 226   |
| 301   |
| 376   |
| 451   |
| 526   |

FIGURE 2B

```
601  ACGTGTTCTCCAAATACCAGTCGACAAAGATGGGTTGTCCTCTTTAAGAAGTTTGATGAAGGCCGGAACAACT
           ValPheSerLysTyrGlnLeuAspLysAspGlyValValLeuPheLysLysPheAspGluGluGlyArgAsnAsnPhe

676  TTGAAGGGGAGGTCACCAAGGAGAGAACCTGCTGGACTTTATCAAACACAACCAGCTGCCCCTTGTCATCGAGTTCA
           GluGlyGluValThrLysGluAsnLeuLeuAspPheIleLysHisAsnGlnLeuProLeuValIleGluPheThr

751  CCGAGCAGACAGCCCCGAAGATTTTTGGAGGTGAAATCAAGACTCACATCCTGCTGTTCTTGCCCAAGAGTGTGT
           GluGlnThrAlaProLysIlePheGlyGlyGluIleLysThrHisIleLeuLeuPheLeuProLysSerValSer

826  CTGACTATGACGGCAAACTGAGCAACTTCAAAACAGCAGCCCGAGAGCTTCAAGGGCAAGATCCTGTTCATCTTCA
           AspTyrAspGlyLysLeuSerAsnPheLysThrAlaAlaGluSerPheLysGlyLysIleLeuPheIleIle

901  TCGACAGGCGACCACCAGCCGACAACCAGCTCGAGTTCTTTGGCCTGAAGAAGGAAGAGTGCCCGGCCGTGC
           AspSerAspHisThrAspAsnGlnArgIleLeuPheGlyLeuLysLysGluCysProAlaValArg

976  GCCTCATCACCTTGGAGGAGGAGATGACCAAGTACAAGCCCGAATCGGAGGAGCTGACGGCAGAGAGGATCACAG
           LeuIleThrLeuGluGluGluMetThrLysTyrLysProGluSerGluGluLeuThrAlaArgIleThrGlu

1051 AGTTCTGCCACCGCTTCCTGGAGGGCAAAATCAAGCCCCACCTGATGAGCCAGGAGCTGCCGGAGACTGGACA
           PheCysHisArgPheLeuGluGlyLysIleLysProHisLeuMetSerGlnGluLeuProGluAspTrpAspLys

1126 AGCAGCCTGTCAAGGTGCTTGTTGGGAAGAACTTTGAAGACGTGGCTTTTGATGAGAAAAAACGTCTTTGTGG
           GlnProValLysValLeuValGlyLysAsnPheGluAspValAlaPheAspGluLysLysAsnValPheValGlu
```

FIGURE 2C

```
1201 AGTTCTATGCCCCATGGTGTGGTCACTGCAAACAGTTGGCTCCCATTTGGGATAAACTGGGAGAGACGTACAAGG
         PheTyrAlaProTrpCysGlyHisCysLysGlnLeuAlaProIleTrpAspLysLeuGlyGluThrTyrLysAsp

1276 ACCATGAGAACATCGTCATCGCCAAGATGGACTCGACTGCCAACGAGGTGGAGGCCGTCAAAGTGCACGGCTTCC
         HisGluAsnIleValIleAlaLysMetAspSerThrAlaAsnGluValGluAlaValLysValHisGlyPhePro

1351 CCACACTCGGGTTCTTTCCTGCCAGTGCCGACAGGACGGTCATTGATTACAACGGGAACGCACGCTGGATGGTT
         ThrLeuGlyPhePheProAlaSerAlaAspArgThrValIleAspTyrAsnGlyGluArgThrLeuAspGlyPhe

1426 TTAAGAAATTCCTAGAGAGCGGTGGCCAAGATGGGGCAGGGGATGTTGACGACCTCGAGAGACCTCGAAGAAGCAG
         LysLysPheLeuGluSerGlyGlyGlnAspGlyAlaGlyAspValAspAspLeuGluAspLeuGluAlaGlu

1501 AGGAGCCAGACATGGAGGAAGACGATGACGAAAGATGAACTGTGAAAGATGAACTGTAATACGCAAAGCCGGACCCGG
         GluProAspMetGluGluAspAspAspGlnLysAlaValLysAspGluLeuSTOP

1576 GCGCTGCCGAGACCCCTCGGGGGCTGCACACCCAGCAGCAGCCAGCACGCCTCCGAAGCCTGCGGCCTCGCTTGAAG

1651 GAGGGCGTCGCCGGAAACCCAAGGAACCTCTCTGAAGTGcggccgcgcgc
                                                  NotI
```

FIGURE 3A

```
     BamHI
  1  gcgcggatccAGGGTAGGAAGTAGCCGCTCCGAGTGGAGGCGACTGGGGCTGAAGAGCGCCGCCCTCTCGTC 76  CCACTTTCCAGGTGTGTGATCCTGTAAAATTAAATCTTCCAAGATGATCTGGTATATATTAATTATAGGAATTCT
                                            MetIleTrpTyrIleLeuIleIleGlyIleIleLeu 151  GCTTCCCCAGTCTTTGGCTCATCCAGGCTTTTTACTTCAATTGGTCAGATGACTGATTTGATCCATACTGAGAA
     LeuProGlnSerLeuAlaHisProGlyPhePheThrSerIleGlyGlnMetThrAspLeuIleHisThrGluLys 226  AGATCTGGTGACTTCTCTGAAAGATTATATTAAGGCAGAAGAGGACAAGTTAGAACAAATAAAAAAATGGGCAGA
     AspLeuValThrSerLeuLysAspTyrIleLysAlaGluGluAspLysLeuGluGlnIleLysLysTrpAlaGlu 301  GAAGTTAGATGGCTAACTAGTACAGCGACAAAGATCCAGAAGGATTGTTGGGCATCCAGTAAATGCATTCAA
     LysLeuAspArgLeuThrSerThrAlaThrLysAspProGluGlyPheValGlyHisProValAsnAlaPheLys 376  ATTAATGAAACGTCTCGAATACTGAGTGGAGTTGGAGAATCTGGTCCTTAAGGATATGTCAGATGGCTTTAT
     LeuMetLysArgLeuAsnThrGluTrpSerGluLeuValLeuLysAspMetSerAspGlyPheIle 451  CTCTAACCTAACCATTCAGAGACCAGTACTTTCTAATGATGAAGATCAGGTTGGGCAGCCAAAGCTCTGTTACG
     SerAsnLeuThrIleGlnArgProValLeuSerAsnAspGluAspGlnValGlyAlaAlaLysAlaLeuLeuArg 526  TCTCCAGGATACCTACAATTTGGATACAGATACCATCTCAAAGGGTAATCTTCCAGGAGTGAAACACAAATCTTT
     LeuGlnAspThrTyrAsnLeuAspThrAspThrIleSerLysGlyAsnLeuProGlyValLysHisLysSerPhe
```

FIGURE 3B

```
601  TCTAACGGCTGAGGACTGCTTTGAGTTGGGCAAAGTGGCCTATACAGAAGCAGATTATTACCATACGGAACTGTG
     LeuThrAlaGluAspCysPheGluLeuGlyLysValAlaTyrThrGluAlaAspTyrTyrHisThrGluLeuTrp

676  GATGGAACAAGCCCTAAGGCAACTGGATGAAGGCCGAGATTTCTACCATAGATAAAGTCTCTGTTCTAGATTATT
     MetGluGlnAlaLeuArgGlnLeuAspGlyGluIleSerThrIleAspLysValSerValLeuAspTyrLeu

751  GAGCTATGCGGTATATCAGCAGGAGACCTGGATAAGGCACTTTTGCTCACAAAGAAGCTTCTTGAACTAGATCC
     SerTyrAlaValTyrGlnGlnGluThrTrpIleArgHisPheAlaLeuLeuLeuThrLysLeuLeuGluLeuAspPro

826  TGAACATCAGAGAGCTAACTTAAAATATTTGAGTATATAATGGCTAAAGAAAAAGATGTCAATAAGTC
     GluHisGlnArgAlaAsnGlyAsnLeuLysTyrPheGluTyrIleMetAlaLysGluLysAspValAsnLysSer

901  TGCTTCAGATGACCAATCTGATCAGAAAACTACACACCAAAGAAAAAGGGGTTGCTGTGGATTACCTGCCAGAGAG
     AlaSerAspAspGlnSerAspGlnLysThrThrProLysLysLysGlyValAlaValAspTyrLeuProGluArg

976  ACAGAAGTACGAAATGTCTGTGCCGTGGGGAGGGTATCAAAATGACCCCTCGGAGACAGAAAAACTCTTTGCCG
     GlnLysTyrGluMetSerValProTrpGlyGluGlyIleLysMetThrProArgArgGlnLysLysLeuPheCysArg

1051 CTACCATGATGGAAACCGTAATCCTAAATTTATTCTGGCTCCAGCTAAACAGGAGGATGAATGGGACAAGCCTCG
     TyrHisAspGlyAsnArgAsnProLysPheIleLeuAlaProAlaLysGlnGluAspGluTrpAspLysProArg

1126 TATTATTCGCTTCCATGATTATTTCTGATGCAGAAATTGAAATCGTCAAAGACCTAGCAAAACCAAGGCTGAG
     IleIleArgPheHisAspIleIleSerAspAlaGluIleGluIleValLysAspLeuAlaLysProArgLeuSer
```

FIGURE 3C

```
1201  CCGAGCTACAGTACATGACCCTGAGACTGGAAAATTGACCACAGCACAGAGTATCTAAGAGTGCCTGCT
      ArgAlaThrValHisAspProGluThrGlyLysLeuThrThrAlaGlnTyrArgValSerLysSerAlaTrpLeu

1276  CTCTGGCTATGAAAATCCTGTGGTGTCTCGAATTAATATGAGAATACAAGATCTAACAGGACTAGATGTTCCAC
      SerGlyTyrGluAsnProValValSerArgIleAsnMetArgIleGlnAspLeuThrGlyLeuAspValSerThr

1351  AGCAGGAGGAATTACAGGTAGCAAATTATGGAGTTGGAGGACAGTATGAACCCCATTTGACTTTGCACGGAAAGA
      AlaGluGluLeuGlnValAlaAsnTyrGlyValGlyGlyGlnTyrGluProHisPheAspPheAlaArgLysAsp

1426  TGAGCCAGATGCTTTCAAAGAGCTGGGGACAGGAGAAATAGAATTGCTACATGGCTGTTTTATATGAGTGATGTC
      GluProAspAlaPheLysGluLeuGlyThrGlyLysIleAlaThrTrpLeuPheTyrMetSerAspValSer

1501  TGCAGGAGGAGCCACTGTTTTCCTGAAGTTGGAGCTAGTGTTTGGCCCAAAAAAGGAACTGCTGTTTTCTGGTA
      AlaGlyGlyAlaThrValPheProGluValAlaSerValTrpProLysProLysGlyThrAlaValPheTrpTyr

1576  TGCAGTGTTTGCCAGTGGAGAAGGAGATTATAGTACACGGCATGCCAGTGCCTGTCCAGTGCTAGTTGGCAACAAATG
      AlaGlyGlyAlaSerGlyGluGlyAspTyrSerThrArgHisAlaAlaCysProValLeuValGlyAsnLysTrp

1651  GGTATCCAATAAATGCTCCATGAACGTGGACAAGAATTCGAAGAGACCTTGTACGTTGTCAGAATTGGAATGACA
      ValSerAsnLysTrpLeuHisGluArgGlyGlnGluPheArgArgProCysThrLeuSerGluLeuGluSTOP

1726  AACAGGCTTCCCTTTTCTCCTATTGTTGTACTCTTATGTGTCTGATATACACATTTCCATAGTCTTAACTTTCA
1801  GGAGTTTACAATTGACTAACACTCCATGATTCAGTCATGAACCTCATCCCATGTTCATCCTGTGGACAATT
1876  GCTTACTTTGTGGGTTCTTTAAAAGTAACACGAAATCATTGCATAAAACCTTAAAGTTCTGTGGTATC
1951  ACAGAAGACAAGGCCAGAGgaattcgcgc
                          EcoRI
```

FIGURE 4A

```
       KpnI
    ggtaCCATGCGCTCCCTGCTTCTCAGCGCCTTCTGCCTTCTGGAGGGGCCCTGGCCGAGGTG
         MetArgSerLeuLeuLeuSerAlaPheCysLeuLeuGluGlyAlaAlaLeuAlaAlaGluVal 82 AAGAAACCTGCAGCCGCAGCAGCTCCTGCACTGCTGGGAGAAGTTGAGCCCAAGGCCCACGCTTGCCGAGCGC
       LysLysProAlaAlaAlaAlaProGlyThrAlaGluGluLysProLysAlaAlaThrLeuAlaGluArg 151 AGCGCCGGCCTGGCTTCAGCTTGTACCAGGCCATGGCCAGTGGAGAACATCCTGGTGTCACCC
       SerAlaGlyLeuAlaPheSerLeuTyrGlnAlaMetAlaLysAspGlnAlaValGluAsnIleLeuValSerPro 226 GTGGTGGTGGCCTCGTCGCTGTCGTGCTCGTTGCTGGGCTGTCGCTCGCTCGCAGGCCAAGGCAGTG
       ValValValAlaSerSerLeuGlyLeuValSerLeuGlyLyLysAlaThrThrAlaSerGlnAlaLysAlaVal 301 CTGAGCGCCGAGCAGCTGCGCGAGGAGGTTGCGCGAGCTGCTGGGCGAGCTGCTGCTCACTCAGCAACTCC
       LeuSerAlaGluGlnLeuArgAspGluGluValHisAlaGlyLeuGlyLeuLeuArgSerLeuSerAsnSer 376 ACGGCCGCAACGTGACCTGGAAGCTGTGACCCAGCTGTACGACCCAGTCAGTGAGCTTCGCTGCTGATGACTTC
       ThrAlaArgAsnValThrTrpLysLeuGlySerArgLeuTyrGlyProSerValSerPheAlaAspAspPhe 451 GTGCGCAGCAGCAAGCAGCACTACAACTGCGAGCACTCCAAGATCAACTTCCGCGACAAGCCAGGCCGCTGCAG
       ValArgSerSerLysGlnHisTyrAsnCysGluHisSerLysIleAsnPheArgAspLysArgArgProLeuGln 526 TCCATCAACGAGTGGGCCGCAGAGCCACCACCGACCAGGTCACCAAGGACTGCCCGAGGTCACCGAGGCCACGGAC
       SerIleAsnGluTrpAlaAlaGlnThrThrAspGlyLysLeuProGluValLysAspValGluArgThrAsp 601 GGGCCCTGTTAGTCAACGCCATGTTCTTCAAGCCACACTGGGATGAGAAATTCCACCACAAGATGGTGGACAAC
       GlyAlaLeuLeuValAlaAsnAlaMetPhePheLysProHisTrpAspGluLysPheHisHisLysMetValAspAsn
```

FIGURE 4B

```
751   CGTGGCTTCATGGTGACTGGTCCTATACCGTGGGTGTCATGATGATGCACCGGACAGGCCTCTACAACTACTAC
      ArgGlyPheMetValThrArgSerTyrThrValGlyValMetMetMetHisArgThrGlyLeuTyrAsnTyrTyr

826   GACGACGAGAAGGAGAAAAGCTGCAAATCGTGGAGATGCCCCTGGCCCACAAGCTCTCCAGCCTCATCATCCTCATG
      AspAspGluLysGluLysLeuGlnIleValGluMetProLeuAlaHisLysLeuSerSerLeuIleIleLeuMet

901   CCCCATCACGTGGAGCCTCTCGAGCGCCTTGAAAAGCTGTAACCAAAGAGCAGCTGAAGATCTGGATGGGAAG
      ProHisHisValGluProLeuGluArgLeuGluLysLeuLeuLeuThrLysGluGlnLeuLysIleTrpMetGlyLys

976   ATGCAGAAGAAGGCTGTTGCCATCTCCTTGCCCAAGGGTGTGGAGGTGACCATGACCCTGCAGAAACACCTG
      MetGlnLysLysAlaValAlaIleSerLeuProLysGlyValValGluValThrHisAspLeuThrHisLeu

1051  GCTGGGCTGGGCCTGACTGAGGCCATTGACAAGGCCAACAAGGCCGACTTGTCACGCATGTCAGGCAAGAAGGACCTG
      AlaGlyLeuGlyLeuThrGluAlaIleAspLysAlaAsnLysAlaAspLeuSerArgMetSerGlyLysLysAspLeu

1126  TACCTGGCCAGCGTGTTCCACGCCCACCCCTTTGAGTTGGACACAGATGGCAACACCCCTTTCATCTTCTAC
      TyrLeuAlaSerValPheHisAlaThrAlaPheGluLeuAspThrAspGlyAsnProPheAspGlnAspIleTyr

1201  GGGCGCGAGGAGCTGCGCAGCCCCAAGCTGTTCTACGCCGACCACCCCTTCATCTTCCTAGTGCGGGACACCAA
      GlyArgGluGluLeuArgSerProLysLeuPheTyrAlaAspHisProPheIlePheLeuValArgAspThrGln

1276  AGCGGCTCCCTGCTATTCATTGGGCGCCTGGTGACAAGGTGACAAGATGGCGAGACGAGTTATAGGGCCTC
      SerGlySerLeuLeuPheIleGlyArgLeuValArgProLysGlyAspLysMetArgAspGluLeuSTOP

1351  AGGGTGCACACAGGATGGCAGGA
```

EXPRESSION OF MANOSE-BINDING PROTEIN IN METHYLOTROPHIC YEAST

FIELD OF THE INVENTION

The present invention relates to expression of Mannose-Binding Protein (hereinafter "MBP") in methylotrophic yeast strains.

BACKGROUND OF THE INVENTION

Several MBP are described in U.S. Pat. No. 5,270,199. Each vertebrate is believed to possess its own form of MBP. MBP is thought to play a role in the disposal of pathogenic organisms. MBP works both by opsonisizing pathogen, and by activating the complement cascade. MBP consists of several monomers that assemble into one larger multimer. The multimeric form of MBP is believed to be necessary to activate the complement cascade.

Currently the only commercial source of MBP is from fractionated blood. Recombinant MBP has been produced by mammalian cell culture (Ezekowitz, U.S. Pat. No. 5,270,199), but yields are relatively low (20 to 40 mg/l) and attainable only at high cost due to the requirement for expensive culture media containing fetal calf serum. Thus, it has been desired in the art to produce MBP in high yields, and inexpensively, without the use of fetal calf serum.

SUMMARY OF THE INVENTION

Accordingly, an object of the present invention is to provide expression of multimeric MBP.

An additional object of the present invention to provide yeast strains that secrete high levels of MBP.

Another object of the present invention to genetically modify yeast strains to provide for increased multimerization of MBP.

These and other objects of the present invention, which will be apparent from the detailed description of the invention provided hereinafter, have been met in one embodiment by a methylotrophic yeast strain which encodes and expresses an MBP gene. Preferably, the yeast strain also encodes and expresses a protein disulfide isomerase (PDI) gene, prolyl-4-hydroxylase (P4H) gene, and heat shock protein 47 (hsp47) gene, and more preferably also the prolyl-4-hydroxylase (P4H) gene.

BRIEF DESCRIPTION OF THE DRAWING

FIGS. 1A–1B show the DNA sequence of MBP, and the corresponding amino acid sequence (SEQ ID NOS:1 and 2, respectively). The secretion signal is in bold.

FIGS. 2A–2C show the DNA sequence of a human PDI PCR product and the corresponding amino acid sequence (SEQ ID NOS:3 and 4, respectively). The secretion signal is in bold, and the synthetic PCR primer sequences are in lowercase.

FIGS. 3A–3C show the DNA sequence of a human P4H PCR product and the corresponding amino acid sequence (SEQ ID NOS:5 and 6, respectively). The secretion signal is in bold, and the synthetic PCR primer sequences are in lowercase.

Figure 5:
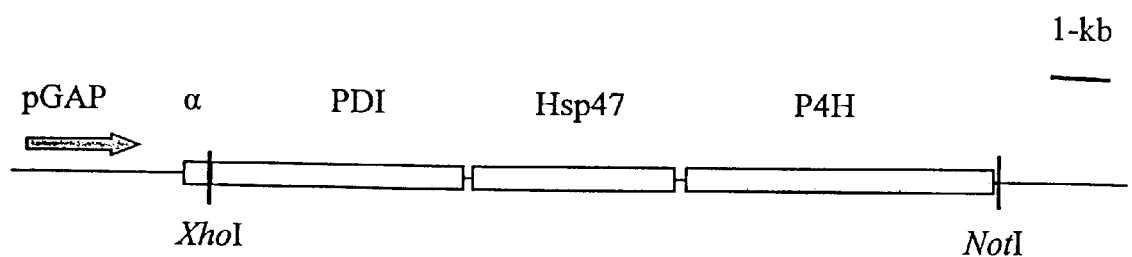

4A–4B show the DNA sequence of a human hsp47 PCR product and the corresponding amino acid sequence (SEQ ID NOS:7 and 8, respectively). The secretion signal is in bold.

FIG. 5 shows the physical map of the PDI-hsp47-P4H cassette, as inserted into plasmid pGAPZαA at the XhoI and NotI sites. The plasmid's pGAP promoter and α-factor secretion signal are indicated.

DETAILED DESCRIPTION OF THE INVENTION

As discussed above, in one embodiment, the above-described objects have been met by a methylotrophic yeast strain which encodes and expresses an MBP gene. Preferably, the yeast strain also encodes and expresses a protein disulfide isomerase (PDI) gene, and heat shock protein 47 (hsp47) gene, and more preferably also the prolyl-4-hydroxylase (P4H) gene.

A methylotrophic yeast strain is one that is able to use methanol as the sole carbon and energy source. Adaptation to growth on methanol is associated with induction of methanol oxidase (alcohol oxidase, AOX), dihydroxyacetone synthase (DAS), and other enzymes of methanol metabolism (Sreekrishna et al, In: *Nonconventional Yeasts in Biotechnology*, Springer, Berlin, page 203 (1996)).

The particular methylotrophic yeast strain employed is not critical to the present invention. Examples of such yeast strains include members of the genera Candida, Kloeckera, Saccharomyces, Rhodotorula, Hansenula, Torulopsis and Pichia (Anthony, *The Biochemistry of Methylotrophs*, page 269 (1982)). Preferred methylotrophic yeast strains are those of the genera Hansenula and Pichia. Particularly preferred methylotrophic yeast strains are *Pichia pastoris* and *Hansenula polymorpha*.

Examples of *Pichia pastoris* which can be employed in the present invention include *Pichia pastoris* GS115 (NRRL Y-15851) (U.S. Pat. No. 4,808,537), *Pichia pastoris* G5190 (NRRL Y-18014) (U.S. Pat. No. 4,818,700), and *Pichia pastoris* PPF1 (NRRL Y-18017) (U.S. Pat. No. 4,812,405). These auxotrophic *Pichia pastoris* strains can be employed in the present invention in view of their ease of selection of recombinants. However, wild-type *Pichia pastoris* strains (e.g., NRRL Y-1 1430 and NRRL Y-1 1431) may also be employed in the present invention if such are transformed with a suitable marker gene, e.g., the SUC2 gene, such that the strains are capable of growth on sucrose, or with an antibiotic resistance gene, such as the Kanamycin gene which confers resistance to G418.

An example of *Hansenula polymorpha* which can be employed in the present invention is *Hansenula polymorpha* (ATCC 34438).

*Pichia pastoris* strain GS115 is the preferred methylotrophic yeast strain employed in the present invention.

To produce the monomeric form of MBP plus some lower multimers, the yeast strain contains an expression cassette comprising the MBP gene under the control of a 5' regulatory region and a 31 termination region, with said cassette present either singly or in multiple copies, incorporated into the yeast genome or in a self-replicating extrachromosomal element. The MBP gene may contain its native secretion signal, or may instead have a heterologous signal sequence added, e.g., the yeast Δ-factor signal (Brake, *Methods Enzymol.*, 185:408 (1990)).

The particular MBP gene employed in the present invention is not critical thereto. Examples of such MBP genes include human MBP gene (FIGS. 1A–1B); a synthetic MBP gene, which may also be codon-optimized for increased expression in a given organism; rat MBP gene (GenBank Accessions M14104 or J02676(SEQ. No. 24); and Drickamer et al, *J. Biol. Chem.*, 261:6878 (1986)); mouse MBP gene (GenBank Accession U09016(SEQ. No. 25); and Sastry et al, *Mamm. Genome*, 6:103 (1995)); and chicken MBP gene (GenBank Accession AF022226(SEQ. No. 26)).

The MBP gene may be obtained by isolation of the gene or synthesized in vitro. For example, an MBP gene can be obtained by screening a human liver cDNA library with oligonucleotide probes or screening a human liver cDNA expression library with anti-MBP antisera to identify MBP expressing human liver cDNAs.

The MBP gene described in U.S. Pat. No. 5,270,199, and deposited under ATCC 67483, is defective and not active in complement activation, since codon 54, normally encoding glycine, contains a single base mutation such that it encodes aspartate (FIGS. 1A–1B). Thus, the correct MBP gene may be derived from ATCC 67483 only after repair of the mutation.

Following the isolation of an MBP gene, the gene is inserted, or two or more MBP genes are inserted in a series, into one or more suitable yeast vectors, such as a plasmid or linear site-specific integrative vector, and used to transform a methylotropic yeast strain.

To produce higher multimers, three additional genes, i.e., protein disulfide isomerase (PDI), proline-4-hydroxylase (P4H), and heat shock protein 47 (hsp47), are co-expressed in the MBP-producing methylotropic yeast strain. These genes are under the control of one or more 5' regulatory regions and 3' termination regions. The PDI, P4H and hsp47 genes may contain their native secretion signals, or may instead have a heterologous signal sequence added, e.g., the yeast Δ-factor signal (Brake, supra).

The PDI, P4H and hsp47 genes may be obtained by PCR cloning from various mammalian cDNA libraries, such as lung or placenta. The human versions of the PDI gene (GenBank Accession X05130; and Pihlajaniemi et al, *EMBO J.*, 6::643 (1987)), the P4H gene (GenBank Accession M24486; Helaakoski et al, *Proc. Natl. Acad. Sci., USA*, 86:4392 (1989)); and the hsp47 gene (GenBank Accession D831754; and Ikegawa et al, *Cytogenet. Cell Genet.*, 71:182 (1995)) are shown in FIGS. 2A–2C, 3A–3C and 4A–4B, respectively.

Once a gene for MBP, PDI, P4H or hsp47 is recovered or constructed, it may be desirable to further tailor the gene, such as fusing to the yeast Δ-factor signal sequence, as discussed in detail below.

In the mature human MBP molecule, the monomeric subunits combine to form trimers, and the trimers multimerize with up to as many as six trimers forming the final MBP molecule (i.e., 18 monomers). The monomers each contain a collagenous stalk attached to a carbohydrate recognition domain (CRD). The collagenous stalk is rich in proline, and some of the prolines are hydroxylated to give hydroxyprolines. Hydroxylation of collagens is carried out by prolyl-4-hydroxylase, which is a heterotetrameric protein comprising two α-subunits, herein referred to as P4H, and two β-subunits, herein referred to as PDI. The PDI subunit can function as a monomer to create disulfide linkages, or in the tetramer with P4H to hydroxylate proline residues (Freedman et al, TIBS., 19:331 (1994)). Recently, human collagen with a stable triple helical structure has been produced upon co-expression with human PDI and P4H genes in a baculovirus system (Lamberg et al, *J. Biol. Chem.*, 271:11988 (1996)). The P4H and PDI function to hydroxylate proline residues in the collagen molecule. It is believed in the present invention that the collagen stalk of MBP undergoes similar processing as collagen. Once the hydroxyprolines on the collagenous stalks of MBP are formed, the stalks can condense into a collagen triple helix. The strands of the triple helix are covalently linked by disulfide bonds.

Though yeast possesses its own PDI gene (Mizunaga et al, *J. Biochem.*, 108:846 (1990)), which catalyzes disulfide bond formation (LaMantia et al, Cell, 74:899 (1993)), it does not have a P4H gene, and is thus unable to form hydroxyprolines. Hence, in the present invention, the gene for human P4H is co-expressed with MBP. Because of concerns that the yeast PDI may be incompatible with the human P4H in forming an active PDI/P4H tetramer, the human PDI gene is also expressed in the present invention. However, there is no requirement for co-expression of the human P4H in the present invention.

In all mammalian tissues that express collagen, heat shock protein 47 (hsp47) is also expressed. hsp47 is considered a collagen-specific molecular chaperone that aids in the proper condensation and folding of the collagen triple helix (Moriyama et al, *Kidney Int.*, 54:110 (1998)). In the present invention it is believed that the expression of hsp47 is required for the efficient production of properly folded higher multimers of MBP. Yeast does not possess a hsp47 gene. Hence, heterologous expression of an hsp47 gene is utilized in the present invention.

Utilizing the present invention, MBP expression levels of about 50 mg of MBP per liter of fermentation broth can been obtained. Thus, the present invention provides a means for the high level secretion of MBP in a low cost shake flask system, and represents a significant advancement over the prior production methods.

Again, to express MBP, the structural gene must be operably linked to one or more 5' regulatory regions and 3' termination sequences, which form expression cassette(s) to be inserted into the host yeast cell via a vector (such as a circular plasmid or linear site-specific integrative vector). The MBP structural gene will have at its 5' end a signal sequence for secretion, comprising either its own native signal sequence or other heterologous signal sequence, such as yeast Δ-factor.

The genes for PDI, P4H and hsp47, each with its own signal sequence, may be placed between a vector's 5' regulatory region and a 3' termination sequence, so that they can all be inserted simultaneously into a host.

The expression "operably linked" as used herein refers to a juxtaposition wherein the gene or gene cluster is linked to a 5' regulatory region and a 3' termination sequence so as to perform their normal function.

The expressions "5' regulatory region" or "promoter" as used herein means DNA sequences which respond to various stimuli and provide controlled rates of mRNA transcription.

The particular promoter employed is not critical to the present invention. Examples of suitable promoters which can be employed in the present invention include the Pichia methanol-inducible methanol oxidase promoter (Stroman et al, U.S. Pat. No. 4,855,231), which is found in pPIC9 and pPIC3; and the constitutively-expressed glyceraldehyde-3-phosphate dehydrogenase promoter (Waterham et al, *Gene*, 186:37 (1997)), which is found in the family of pGAP vectors.

The expression "3' termination sequences" as used herein means sequences 3' to the stop codon of a structural gene which function to terminate, polyadenylate, and to stabilize the mRNA transcription product of the gene to which the sequence is operably linked (such as sequences which elicit polyadenylation).

The particular 3' termination sequence employed is not critical to the present invention. An example of a suitable 3' termination sequence is the 3' AOX1 transcription termination fragment, which is found in vectors such as pPIC3, pPIC9 and pGAPZαA (Invitrogen, Carlsbad, Calif.)

Plasmid-type vectors have long been one of the basic elements employed in recombinant DNA technology. Plasmids are circular extra-chromosomal double-stranded DNA found in microorganisms. Plasmids have been found to occur in single or multiple copies per cell. Included in plasmid DNA is the information required for plasmid reproduction and maintenance within a cell, plus regulatory regions for the expression of cloned genes.

The preferred 5' regulatory regions for the expression of MBP are those that respond to the presence of methanol in the media, as disclosed by Stroman et al, U.S. Pat. No. 4,808,537, which is incorporated herein by reference in its entirety. The sequences disclosed by Stroman et al, supra, provide a suitable means for maintaining plasmids in *Pichia pastoris*. Additionally one or more means of phenotypically selecting the plasmid in transformed cells may also be included in the information encoded in the plasmid.

In the present invention, it is preferred that the pPIC9 vector be used for the MBP gene; and the pGAPZαA vector be used for the PDI, P4H and hsp47 genes to ensure optimal linking to the 3' ends and to the 5' regulatory regions of these vectors using common restriction and ligating enzymes.

The pPIC9 vector contains the yeast Δ-factor secretion signal operably linked to a 948 bp fragment of the yeast alcohol oxidase promoter (AOX1), which allows a gene cloned in frame to the Δ-factor signal to be expressed and secreted under the control of methanol. 3' of the gene insertion site, pPIC9 also contains the 334 bp 3' AOX1 transcriptional terminator, followed by the his4 gene, which is used as a selectable marker when introduced into a his4 auxotrophic yeast strain (e.g., GS115). Next, there follows a 758 bp portion of the 3' region of AOX1 which, along with the 5' AOX1 promoter region, allows for recombination into the host AOX1 gene. Recombination may also occur between the vector his4 gene and the host his4 gene. Finally, pPIC9 contains an ampicillin resistance gene, which is used for selection and maintenance of the vector in *E. coli*.

The pPIC3 vector may also be used and is similar to pPIC9, except the yeast Δ-factor signal sequence is absent, and thus any gene that is expressed must carry its own signal sequence if it is to be secreted.

The pGAPZαA vector contains a yeast Δ-factor secretion signal, cloning site for an in-frame fusion, plus a 3' AOX1 transcriptional terminator, all similar to pPIC9, except that expression is under control of a 483 bp glyceraldehyde-3-phosphate dehydrogenase promoter region (pGAP), which also serves as the site for recombination into the yeast genome. A Zeocin resistance gene serves as the selectable marker in this vector.

Again, the particular 3' termination sequence is not critical to the present invention, nor is the particular promoter or secretion signal, as any promoter/signal combination that functions in yeast to express proteins to high levels is adequate. Other well-known vectors that may be used in the present invention include pHIL-S1 (AOX1 promoter, pho1 secretion signal, his4 gene); pHIL-D2 (AOX1 promoter, no signal sequence, his4 gene); pGAPZ A, PGAPZ B, and PGAP C (pGAP promoter, no signal sequence, Zeocin resistance, three different cloning frames); and pGAPZαB and pGAPZαC (same as pGAPZαA, but cloning site in different reading frames) (Invitrogen).

Suitable integrative vectors for use in the present invention are the site-specific integrative vectors described by Stroman et al, supra, which include PSAOH 10, pTAFH 85, pT76H 2 and pT76H 3. An integrative vector has no yeast origin of replication. Thus, yeast transformants can only be isolated if recombination occurs between the plasmid and the yeast genome. These vectors comprise a serially arranged sequence of at least:

(1) a first insertable DNA fragment;
(2) a selectable marker gene; and
(3) a second insertable DNA fragment.

An expression cassette containing a heterologous structural gene is inserted in this vector between the first and second insertable DNA fragments either before or after the marker gene. Alternatively, an expression cassette can be formed in situ if a regulatory region or promoter is contained within one of the insertable fragments to which the structural gene may be operably linked.

The first and second insertable DNA fragments are each at least about 200 nucleotides in length, and have nucleotide sequences which are homologous to portions of the genomic DNA of the species to be transformed. The various components of the integrative vector are serially arranged forming a linear fragment of DNA such that the expression cassette and the selectable marker gene are positioned between the 3' end of the first insertable DNA fragment and the 5' end of the second insertable DNA fragment. The first and second insertable DNA fragments are oriented with respect to one another in the serially arranged linear fragment as they are oriented in the parent genome.

Nucleotide sequences useful as the first and second insertable DNA fragments are nucleotide sequences which are homologous with separate portions of the native genomic site at which genomic modification is to occur. For example, if genomic modification is to occur at the locus of the alcohol oxidase gene, the first and second insertable DNA fragments employed is homologous to separate portions of the alcohol oxidase gene locus. Examples of nucleotide sequences which could be used as first and second insertable DNA fragments are DNA sequences such as the *Pichia pastoris* alcohol oxidase (AOX1) gene and his4 gene. The AOX1 gene and his4 gene are disclosed in Stroman et al, U.S. Pat. Nos. 4,855,231 and 4,885,242, both of which are incorporated herein by reference in their entirety.

In a preferred embodiment of the present invention, the first DNA fragment of AOX1 contains an operable regulatory region which comprises the regulatory region utilized in the expression cassette for MBP. Optionally, an insertion site or sites and a 3' termination sequence may be placed immediately 3' to the first insertable DNA fragment. This conformation of the linear site-specific integrative vector has the additional advantage of providing a ready site for insertion of a structural gene without necessitating the separate addition of a compatible 3' termination sequence.

In a preferred embodiment of the present invention, the first DNA fragment of the GAP gene of plasmid pGAPZαA contains an operable regulatory region utilized by the expression cassette for the PDI, hsp47 and P4H genes. The GAP gene is the first insertable DNA region in the vector. The second DNA fragment of AOX1 comprises the second insertable DNA site.

If the first insertable DNA fragment does not contain a regulatory region, a suitable regulatory region can be inserted 5' to the structural gene, in order to provide an operable expression cassette. Similarly, if no 3' termination sequence is provided at the insertion site to complete the expression cassette, a 3' termination sequence can be operably linked to the 3' end of the structural gene.

It is also desirable to include at least one selectable marker gene in the DNA used to transform the host yeast strain. This facilitates selection and isolation of those microorganisms which have incorporated therein the transforming DNA. The marker gene confers a phenotypic trait to the transformed microorganism which the host does not have, e.g., restoration of the ability to produce a specific amino acid where the untransformed host strain has a defect in the specific amino acid biosynthetic pathway, or provides resistance to antibiotics and the like. The particular selectable marker gene employed is not critical to the present invention. Examples of selectable marker genes include the his4 gene (U.S. Pat. No. 4,885,242) and the arg4 gene (U.S. Pat. No. 4,818,700) from *Pichia pastoris* and *Saccharomyces cerevisiae*, the invertase gene (SUC2) (U.S. Pat. No. No. 4,857,467) from *Saccharomyces cerevisiae*, or the G418/kanamycin resistance gene from the *E. coli* transposable elements Tn601or Tn903 (Oka et al, *J. Mol. Biol.*, 147:217 (1981), GenBank accessions V00359 and J01839); or the Zeocin resistance gene, as in pGAPZαA.

Additional DNA sequences can also be incorporated into the vectors employed in the present invention, such as, for example, bacterial plasmid DNA, bacteriophage DNA, and the like. Such sequences enable the amplification and maintenance of these vectors in bacterial hosts.

The insertion of the genes of the present invention into suitable vectors may be accomplished by any suitable technique which cleaves the chosen vector at an appropriate site or sites and results in at least one operable expression cassette containing the desired gene being present in the vector. Ligation of the desired gene may be accomplished by any appropriate ligation technique, such as utilizing T4 DNA ligase.

The initial selection, propagation and optional amplification of the ligation mixture of the desired gene and a vector is preferably performed by transforming the mixture into a bacterial host, such as *E. coli* (although the ligation mixture could be transformed directly into a yeast host, but the transformation rate would be extremely low). Suitable transformation techniques for *E. coli* are well-known in the art (Hanahan, In: DNA Cloning, Volume I, A Practical Approach, IRL Press, Oxford, page 109 (1985)). Additionally, selection markers and bacterial origins of replication necessary for the maintenance of a vector in a bacterial host are also well-known in the art (Goeddel et al, *Methods in Enzymol.*, Vol. 185 (1990)). The isolation and purification of the desired plasmid containing the desired gene in an expression system may be accomplished by any suitable means for the separation of plasmid DNA from the host DNA. Similarly the vectors formed by ligation may be tested, preferably after propagation, to verify the presence of the desired gene and its operable linkage to a regulatory region and a 3' termination sequence. This may be accomplished by a variety of techniques including endonuclease digestion, gel electrophoresis and Western immuno-blot.

Transformation of plasmids or linear vectors into yeast hosts may be accomplished by suitable transformation techniques such as those taught by Stroman et al, U.S. Pat. Nos. 4,808,537 and 4,879,231; Cregg et al, U.S. Pat. No. 4,929,555; Hinnen et al, *Proc. Natl. Acad. Sci.*, 75:1929 (1978); Ito et al, *J. Bacteriol.*, 153:163 (1983); Cregg et al, *Mol. Cell Biol.*, 5:3376 (1985); and Sreekrishna et al, Gene, 59:115 (1987). Preferable for the practice of the present invention is the transformation technique of Stroman et al, U.S. Pat. No. 4,808,537.

It is desirable in the present invention to utilize linearized vectors for yeast transformation and to screen for insertions by Western immuno-blot.

After successful insertion of the plasmid, such as pPIC9, containing the MBP gene via one of the methods described above, the same procedures can be repeated to insert the PDI, P4H and hsp47 genes first into a vector, such as pGAPZαA, and then into a yeast clone containing the MBP gene. A preferred embodiment for insertion of these genes requires verification for each gene, a Western immuno-blot for each of PDI and hsp47, and examination of the PDI Western immuno-blot for PDI multimerization as an indicator that P4H is present and in the correct association with PDI.

Transformed yeast cells can be selected for by using appropriate techniques such as culturing previously auxotrophic cells after transformation in the absence of the biochemical product required (due to the cell's auxotrophy), selection for and detection of a new phenotype ("methanol slow"), or culturing in the presence of an antibiotic which is toxic to the yeast in the absence of a resistance gene contained in the transformant.

Isolated transformed yeast cells are cultured by appropriate fermentation techniques such as shake flask fermentation, high density fermentation or the technique disclosed by Cregg et al, *Pichia Pastoris*, 5(Bio/Technology):479 (1987). Isolates may be screened by assaying for MBP production to identify those isolates with the highest MBP production level, and more specifically for the highest level of MBP multimer production. The degree of multimerization of MBP can be assessed by SDS/polyacrylamine gel electrophoresis (SDS/PAGE) of the protein in the absence of a reducing agent, such as β-mercaptoethanol. Such a gel will resolve monomers, dimers, trimers, and the various higher multimers (Kurata et al, *J. Biochem.*, 115:1148 (1994)).

The following examples are provided for illustrative purposes only, and are in no way intended to limit the scope of the present invention.

Suitable techniques for the recombinant DNA procedures described below may be found in, e.g., *Methods in Enzymology*, Orlando, Fla., Academic Press, Inc., particularly Volume 152, published as, Berger et al, *Guide to Molecular Cloning Techniques*, Orlando, Fla., Academic Press, Inc. (1987) and Sambrook et al, *Molecular Cloning/A Laboratory Manual*, 2d ed., Cold Spring Harbor Laboratory Press (1989), which are all hereby incorporated by reference herein in their entirety. Techniques for genetic manipulations and protein expression in Pichia described below may be found in *Methods in Molecular Biology*, Totowa, N.J., Humana Press, particularly Volume 103, published as, *Pichia Protocols*, Higgins et al, Humana Press (1998), and the Instruction Manuals published by Invitrogen Corp. (San Diego, Calif.) entitled *Pichia Expression Kit Version B*; and pGAPZ A, B and C, pGAPZαA, B and C, Version A, which are all hereby incorporated by reference herein in their entirety.

EXAMPLE 1

Native MBP Gene

A mutant version of the MBP gene is publically available from the American Type Culture Collection (Accession ATCC 67483), having the sequence shown in FIGS. 1A–1B. However, this MBP gene has a mutation in codon 54, such that the native glycine codon "GGC" is converted to an aspartate codon "GAC". The mutation was repaired using the PCR method described in *PCR Primer, A Laboratory Manual*, Dieffenbach et al, Eds., Cold Spring Harbor Laboratory, Cold Spring Harbor, N.Y., pages 603–612 (1995). The following sense and antisense end primers were used: MBP-5: GCGC GAATTCACCATGGCCCTGTTTCCATCACTC (SEQ ID NO:9) (which has an EcoRI site underlined, and a start codon in bold) and MBP-3: CAAGG GCGGCCGCAGTGATATGACCCTTCA (SEQ ID NO:10)

(which has a NotI site underlined, and a stop codon in bold), respectively. Primer MBP-5 was designed to change the ribosome binding site, the so-called Kozak site (Kozak, *Nucleic Acids Res.*, 15:8125 (1987); and Kozak, *Proc. Natl. Acad. Sci.*, 87:8301 (1990)), to the optimized nucleotide sequence ANN<u>ATG</u>G (SEQ ID NO:11), as recommended by Invitrogen for Pichia expression (the translational initiating Met codon (ATG) is underlined, and nucleotides "IN" can be anything). The following sense and antisense overlapping repair primers were used:

MBP-55: GCTTCCCAGGCAAAGATGGGCGTGAT<u>GGC</u>ACCAAGGGAGA (SEQ ID NO:12) and

MBP-34: CTTGGCCTGGTTCCCCCTTTTCTCCCT-TGGT<u>GCC</u>ATCACG (SEQ ID NO:13), respectively. In MBP-55 and MBP-34, codon 54 is underlined.

Recombinant Taq DNA polymerase (Boehringer-Mannheim, Indianapolis, Ind.) was used to carry out the PCR using an Idaho Technology Rapidcycler thermal cycler (Idaho Technology Inc., Idaho Falls, Id.). The manufacturer's recommendations were followed with slight modifications. Each 10 μl reaction mixture included 10 pmol of each primer and approximately 10 pmol of template DNA (plasmid from ATCC 67483). The reaction mixtures were incubated at 94° C. for 15 sec before cycle 1. Each of the subsequent 30 cycles consisted of 0 sec at 940° C., 0 sec at 55° C., and 40 sec at 74° C. per kb of template to be amplified between the primers. After the last cycle the polymerization step was extended by 5 min at 74° C. to complete synthesis of all strands.

The final PCR product comprising the repaired gene was cloned into yeast vector pPIC3 for expression (see Example 2).

In addition, the repaired MBP gene was re-amplified via PCR using the following sense and antisense primer pair: MBP-4 GCGC<u>CTCGAG</u>AAAAGAGAAACTGTGACCTGTGAG (which has an XhoI site underlined) (SEQ ID NO:14) and MBP-3, respectively, giving a product that encoded the mature MBP polypeptide but without a signal sequence. This PCR product was cloned into yeast vector pPIC9 for expression using the yeast Δ-factor secretion signal (see Example 2).

EXAMPLE 2

Expression Cloning of the Native MBP Gene

The repaired MBP gene with its native secretion signal sequence (PCR product MBP-5/MBP-3 from Example 1) was end-trimmed via EcoRI/NotI digestion, and cloned in its entirety into yeast vector pPIC3.

The mature portion of the MBP gene (PCR product MBP-4/MBP-3 from Example 1, which lacks a signal sequence) was end-trimmed via XhoI/NotI digestion, and cloned into yeast secretion vector pPIC9 as a fusion to the yeast Δ-factor secretion signal.

For the cloning, the yeast vectors were digested with the same enzymes as the DNA to be inserted (EcoRI/NotI for cloning the entire gene into pPIC3) and, XhoI/NotI for cloning the mature protein cassette into pPIC9). Insertion was accomplished using T4 DNA ligase. The ligation products were used to transform *E. coli* strain XL1-Blue, and the desired transformants were selected and verified using standard techniques. DNA from the *E. coli* transformants was isolated, linearized by digestion with the enzyme SacI, and transformed via electroporation into P. pastoris strain GS115 (his4) NRRL Y-15851, using standard techniques. Transformed cells were plated onto minimal dextrose medium (MDM) comprising 13.4 g of yeast nitrogen base with ammonium sulfate and without amino acids, 400 μg biotin, 10 g dextrose (glucose), 15 g agar, and water to 1.0 liter, for selection of His⁺ recombinants.

After several days of growth on MDM plates, the His⁺ colonies were screened for MBP production via colony hybridization. To this end, colonies were lifted onto nitrocellulose filters, which were placed onto minimal methanol medium (MMM) plates comprising 13.4 g of yeast nitrogen base with ammonium sulfate and without amino acids, 400 μg biotin, 5.0 ml methanol, 15 g agar, and water to 1.0 liter. The methanol in the MMM medium induced the AOX1 promotor in the integrated pPIC9 or pPIC3 construction, thus forcing MBP expression and secretion onto the filters. After 1–3 days incubation at 30° C., the filters were washed with Tris-buffered saline Tween (TBST) comprising 8.0 g NaCl, 0.2 g KCl, 3.0 g Tris, water to 1.0 liter, adjusted with HCl to pH 7.0 and 0.2 ml of Tween 20 per liter, treated for 30 min with blocking solution comprising 1.5% (w/v) Blocking Reagent (Boehringer Mannheim Gmbh, Germany) in TBS (see below), and incubated for several hours with anti-MBP antibody (mouse monoclonal, supplied by Accurate Chemical & Scientific Corp., Westbury, N.Y.), diluted to 1/2500 in TBS. The filters were then washed with Tris-buffered saline (TBS) comprising 8.0 g NaCl, 0.2 g KCl, 3.0 g Tris, water to 1.0 liter, adjusted with HCl to pH 7.4, and incubated for at least 1 hr in anti-mouse-APase antibody (goat anti-mouse IgG alkaline phosphatase conjugate (whole molecule), supplied by Sigma, St. Louis, Mo.), diluted to 1/30,000 in TBS. The filters were then washed in TBS followed by alkaline phosphatase buffer (APase buffer) comprising 100 mM NaCl, 10 mM $MgCl_2$, 100 mM Tris (pH 9.5), and developed with APase developing solution comprising 5.5 mg 5-bromo-4-chloro-3-indolyl phosphate (BCPIP), and 5.5 mg 4-nitro blue tetrazolium chloride (NBT) in 20 ml of APase Buffer. Colonies that produced dark purple spots, indicative of MBP secretion, were selected for further evaluation. It is believed that increased levels of MBP expression (judged by intensity of purple spots on filter) are caused by spontaneous multiple insertions of the expression cassette into the Pichia genome.

Selected Pichia clones containing pPIC3::MBP or pPIC9::MBP were cultured in shake flasks of buffered minimal glycerol-complex medium (BMGY) comprising 100 ml of potassium phosphate buffer (pH 6.0) per liter, 13.4 g of yeast nitrogen base with ammonium sulfate and without amino acids per liter, 400 μg of biotin per liter, 10.0 ml of glycerol per liter, 10 g of yeast extract per liter, 20 g of peptone per liter, without agar as starter cultures, which were used to inoculate shake flask cultures in buffered minimal methanol-complex medium (BMMY) comprising 100 ml of potassium phosphate buffer (pH 6.0) per liter, 13.4 g of yeast nitrogen base with ammonium sulfate and without amino acids per liter, 400 μg of biotin per liter, 5.0 ml of methanol per liter, 10 g of yeast extract per liter, 20 g of peptone per liter, to assess MBP production. Cultures comprised 50 ml medium in 2.0 liter baffled Erlenmeyer flasks, and were shaken at 18–22° C. Twice each day at each subsequent day's growth, another 0.25 ml of methanol was added. Each day over 4 days of growth, 2.0 μl of culture medium were spotted onto nitrocellulose filters. These spot blots were treated with blocking solution, and developed as per the colony lifts discussed above. A dilution series of authentic MBP (1–100 μg/ml, from expression of the MBP gene in CHO cell tissue culture, isolated by Dr. Alan Ezekowitz, Boston Children's Hospital) was spotted as a standard, against which the unknown spots were compared. Under these conditions, MBP levels increased through day 4, with the best clones yielding 40–50 mg MBP per liter. One such clone, designated S3, which contains the pPIC9::MBP construction, was deposited on Nov. 24, 1998, at the American Type Culture Collection under ATCC No. 74474.

Culture supernatants from S3 were subjected to SDS-polyacrylamide electrophoresis (Laemmli, Nature, 277:680 (1970)) after mixing with an equal volume of 2X SDS/PAGE treatment buffer comprising 0.125 M Tris, 4.0% (w/v) sodium dodecyl sulfate (SDS), 20% (v/v) glycerol, without 10% (v/v) β-mercaptoethanol (to denature protein but maintain disulfide-linked multimers) or with 10% (v/v) β-mercaptoethanol (to denature and reduce multimers to monomers). Gels were subjected to overnight electrotransfer onto nitrocellulose filters in 10% (v/v) methanol transfer buffer comprising 3.05 g Tris, 14.4 g glycine, 100 ml methanol, and water up to 1 liter, using standard methodology. The filter was treated with blocking solution, and developed for MBP as per the colony lifts and spot blots discussed above. Expression of MBP in S3 was revealed as a ladder of multimers, with dimer being the most intense band, with lesser monomer, and lesser still of trimer and tetramer.

EXAMPLE 3

Co-Expressing MBP With PDI, P4H and Hsp47 Genes

The human PDI gene (FIGS. 2A–2C) was obtained by PCR amplification of a human lung cDNA library using the following sense and antisense primer pair: PDI-1 GCGC GAATTCTGCTCCGTGTCCGACATGCT (SEQ ID NO:15) (which has a BamHI site underlined and a start codon in bold), PDI-2 GCGC GCGGCCGCACTTCAGAGAGGTTCCTTGG (SEQ ID NO:16) (which has a NotI site underlined), respectively. The human lung cDNA library used was human lung cDNA cloned into λTriplEx, from QUICK-Screen Human cDNA Library Panel (Clontech Laboratories, Inc.). The resulting product was cloned into the SrfI site of E. coli vector pCR-Script. As it was desired to express the PDI mature polypeptide as a fusion to the yeast Δ-factor secretion signal using vector pGAPZαA, the necessary in-frame 5' -XhoI restriction site, plus 3' -KpnI site, were introduced by further PCR of the pCR-Script clone using the following sense and antisense primers: PDI-12 CTCGAGAAGAGAGACGCCCCCGAGGAGGAGGACCA (SEQ ID NO:17) (which has an XhoI site underlined) and PDI-13 GGTACCTTACAGTTCATCTTTCACAGC (SEQ ID NO:18) (which has a KpnI site underlined), respectively. The resulting PCR product was cloned into the XhoI/NotI site of pGAPZαA. After linearization with AvrII and electroporation into P. pastoris clone S3 (expressing MBP), the cells were plated onto YEPD/Zeocin comprising 10 g of yeast extract per liter, 20 g of peptone per liter, 20 g of dextrose per liter, 15 g of agar per liter and 100 μg of Zeocin per ml.

Expression of PDI was verified by colony hybridization and development with anti-PDI antibody (mouse monoclonal, supplied by Dako A/S, Denmark), diluted to 1/2000 in TBS, as per the MBP colony lifts (see Example 2).

The human P4H gene (FIGS. 3A–3C) was obtained by PCR amplification of a human placenta cDNA library using the following sense and antisense primer pair: P4H-1 GCGC GGATCCAGGGTAGGAAGTAGCCGCTC (SEQ ID NO:19) (which has a BamHI site underlined) and P4H-2 GCGCGAATTCCTCTGCCTTGTCTTCTGTGA (SEQ ID NO:20) (which has an EcoRI site underlined, respectively. The human placenta cDNA library used was QUICK-Clone Human Placenta cDNA (Clontech Laboratories, Inc., Palo Alto, Calif.). The resulting product was cloned into the SrfI site of E. coli vector pCR-Script such that the P4H gene was oriented with the P4H-1 primer end toward the NotI site of the vector, and the P4H-2 primer end toward the KpnI site of the vector. The resulting P4H cassette was excised with KpnI/NotI and cloned in series with the PDI gene in vector pGAPZαA into the KpnI/NotI site, using techniques standard in the art.

Expression of P4H was verified indirectly by its effect on multimerization of the PDI gene product. That is, extracts from P. pastoris clones S3(pGAPZαA::PDI) and S3(pGAPZαA::PDI-P4H) were subjected to polyacrylamide gel electrophoresis as described for MBP (Example 2) except both SDS and β-mercaptoethanol were omitted from all solutions (i.e., a native gel), to prevent dissociation of PDI/P4H multimers. The gel was electroblotted onto nitrocellulose, treated with blocking solution, and developed with anti-PDI antibody as per the PDI colony lifts above. The clone containing both the PDI and P4H genes produced three bands at higher apparent molecular weights than the clone expressing PDI alone, indicating that P4H was expressed and the product formed multimers with the PDI.

The human Hsp47 gene (FIGS. 4A–4B) was obtained by PCR amplification of a human lung cDNA library using the following sense and antisense primer pair: Hsp47-11 GGTACCATGCGCTCCCTCCTGCTTCTCAGCGCCTTC TGCCTCCTGG (SEQ ID NO:21) (which has a KpnI site underlined and a start codon in bold) and Hsp47-10 TCCT-GCCATCCTGTGTGCACCCTGA (SEQ ID NO:22), respectively. The resulting product was cloned into E. coli vector pCR-Script, oriented such that the Hsp47-10 primer end was toward the KpnI site of pCR-Script (the opposite end possesses its own KpnI site, from primer Hsp47-11). Primer Hsp47-11 also contains the improved Kozak sequence ANNATGG (SEQ ID NO:23) which straddles the ATG translational start codon (bold), to increase expression over the native sequence. The resulting Hsp47 cassette was excised from pCR-Script as a KpnI fragment and cloned in between the PDI and P4H genes in vector pGAPZαA, at the KpnI site, using techniques standard in the art.

FIG. 5 shows a physical map of the final pGAPZαA::PDI-Hsp47-P4H construction, which was linearized by digestion with AvrII and electroporated into P. pastoris clone S3, which expresses MBP (from Example 2). After plating cells onto YEPD/Zeocin, clones expressing PDI were screened using colony lifts and processing with anti-PDI antibody, as described above, or with anti-Hsp47 antibody (Mouse monoclonal, supplied by StressGen Biotech., Victoria, BC, Canada), diluted to 1/2700 in TBS.

The selected clone AF5, which produced a dark purple spot in the colony hybridization, was cultured at 23° C. in 2 liter shake flasks in 50 ml buffered minimal methanol medium (BMMM) plus ascorbate/α-ketoglutarate comprising 100 ml of potassium phosphate buffer (pH 3.0) per liter, 13.4 g of yeast nitrogen base with ammonium sulfate and without amino acids per liter, 400 μg of biotin per liter, 5.0 ml of methanol per liter, 200 mg of ascorbic acid per liter, and 200 mg of α-ketoglutaric acid per liter. Ascorbic acid and α-ketoglutarate were added, since these are required by the PDI/P4H complex to carry out the proline hydroxylation reaction (Kivirikko et al, Adv. Enzymol. Relat. Areas Mol. Biol., 72:325 (1998)). Twice each day at each subsequent day's growth, another 200 mg per liter of ascorbic acid, 200 mg of α-ketoglutaric acid per liter and 5.0 ml of methanol per liter were added. Culture supernatants at day 2 were subjected to SDS/PAGE followed by electroblotting and development for MBP, as described in Example 2. Increased formation of higher MBP multimers was observed when MBP was co-expressed with the PDI-Hsp47-P4H cassette.

Cloned AF5, which contains the pPIC9::MBP construction, as well as the pGAPZαA::PDI-Hsp47-P4H construction, was deposited on Nov. 24, 1998, at the American Type Culture Collection under ATCC No. 74475.

While the invention has been described in detail, and with reference to specific embodiments thereof, it will be apparent to one of ordinary skill in the art that various changes and modifications can be made therein without departing from the spirit and scope thereof.

What is claimed:

1. A methylotrophic yeast strain which comprises a DNA molecule which encodes mannose-binding protein (MBP), a DNA molecule which encodes protein disulfide isomerase (PDI), a DNA molecule which encodes heat shock protein 47 (hsp47), and a DNA molecule which encodes prolyl-4-hydroxylase (P4H), wherein upon culturing, said yeast strain produces said MBP, PDI, hsp47 and P4H.

2. The methylotrophic yeast strain of claim 1, wherein said yeast strain is a member of a genera selected from the group consisting of Candida, Kloeckera, Saccharomyces, Rhodotorula, Hansenula, Torulopsis and Pichia.

3. The methylotrophic yeast strain of claim 1, wherein said yeast strain comprises an expression cassette comprising a *P. pastoris* AOX1 5' regulatory region operably linked to a yeast α-factor secretion signal sequence having a 5' terminal ATG start codon, which is fused in-frame to said DNA molecule which encodes MBP, which is operably linked to a 3' termination sequence.

4. The methylotrophic yeast strain of claim 1, wherein said yeast strain comprises an expression cassette comprising a *P. pastoris* AOX1 5' regulatory region operably linked to a MBP secretion signal sequence having a 5' terminal ATG start codon, which is fused in-frame to said DNA molecule which encodes MBP, which is operably linked to a 3' termination sequence.

5. The methylotrophic yeast strain of claim 1, wherein said MBP is encoded by a DNA molecule comprising a DNA sequence selected from the group consisting of SEQ ID NO:1; SEQ ID NO:24; SEQ ID NO:25; and SEQ ID NO:26.

6. The methylotrophic yeast strain of claim 1, wherein said PDI comprises amino acids 1-508 of SEQ ID NO:4.

7. The methylotrophic yeast strain of claim 1, wherein said hsp47 comprises amino acids 1-418 of SEQ ID NO:8.

8. The methylotrophic yeast strain of claim 1, wherein said P4H comprises amino acids 1-534 of SEQ ID NO:6.

9. The methylotrophic yeast strain of claim 1, wherein said yeast strain is obtained by transforming strain S3 with a DNA molecule which encodes MBP, a DNA molecule which encodes PDI, a DNA molecule which encodes hsp47, and a DNA molecule which encodes P4H.

10. The methylotrophic yeast strain of claim 1, wherein said strain is strain AF5 (ATCC No. 74475).

11. The methylotrophic yeast strain of claim 2, wherein said yeast strain is a member of a genera selected from the group consisting of Hansenula and Pichia.

12. The methylotrophic yeast strain of claim 11, wherein said yeast strain is *Pichia pastoris* or *Hansenula polymorpha*.

13. The methylotrophic yeast strain of claim 12, wherein said *Pichia pastoris* is selected from the group consisting of *Pichia pastoris* GS115, *Pichia pastoris* G5190, and *Pichia pastoris* PPF1.

14. The methylotrophic yeast strain of claim 12, wherein said yeast strain is *Hansenula polymorpha*.

15. The methylotrophic yeast strain of claim 13, wherein said *Pichia pastoris* is GS115.

16. A method for producing MBP comprising culturing the methylotropic yeast strain of claims 1, 2, 11, 12, 13, 15, 14, 3, 4, 5, 6, 7, 8, 9, or 10, under conditions whereby MBP is produced and secreted by said yeast.

* * * * *

SEQUENCE LISTING

<160> NUMBER OF SEQ ID NOS: 26

<210> SEQ ID NO 1
<211> LENGTH: 900
<212> TYPE: DNA
<213> ORGANISM: Human

<400> SEQUENCE: 1

```
ggtaaatatg tgttcattaa ctgagattaa ccttccctga gttttctcac accaagtga      60 ggaccatgtc cctgtttcca tcactccctc tccttctcct gagtatggtg gcagcgtctt    120
actcagaaac tgtgacctgt gaggatgccc aaaagacctg ccctgcagtg attgcctgta    180
gctctccagg catcaacggc ttcccaggca agatgggcg tgatggcacc aagggagaaa    240 aggggaacc aggccaaggg ctcagaggct tacagggccc cctggaaag ttggggcctc      300 caggaaatcc agggccttct gggtcaccag gaccaaaggg ccaaaaagga gaccctggaa    360
aaagtccgga tggtgatagt agcctggctg cctcagaaag aaaagctctg caaacagaaa    420
tggcacgtat caaaaagtgg ctgaccttct ctctgggcaa acaagttggg aacaagttct    480
tcctgaccaa tggtgaaata atgacctttg aaaaagtgaa ggccttgtgt gtcaagttcc    540
aggcctctgt ggccaccccc aggaatgctg cagagaatgg agccattcag aatctcatca    600
aggaggaagc cttcctgggc atcactgatg agaagacaga agggcagttt gtggatctga    660
caggaaatag actgacctac acaaactgga acgagggtga acccaacaat gctggttctg    720
atgaagattg tgtattgcta ctgaaaaatg gccagtggaa tgacgtcccc tgctccacct    780
cccatctggc cgtctgtgag ttccctatct gaagggtcat atcactcagg ccctccttgt    840
ctttttactg caacccacag gcccacagta tgcttgaaaa gataaattat atcaatttcc    900
```

<210> SEQ ID NO 2
<211> LENGTH: 248
<212> TYPE: PRT
<213> ORGANISM: Human

<400> SEQUENCE: 2

```
Met Ser Leu Phe Pro Ser Leu Pro Leu Leu Leu Leu Ser Met Val Ala
 1               5                  10                  15

Ala Ser Tyr Ser Glu Thr Val Thr Cys Glu Asp Ala Gln Lys Thr Cys
            20                  25                  30

Pro Ala Val Ile Ala Cys Ser Ser Pro Gly Ile Asn Gly Phe Pro Gly
        35                  40                  45

Lys Asp Gly Arg Asp Gly Thr Lys Gly Glu Lys Gly Glu Pro Gly Gln
    50                  55                  60

Gly Leu Arg Gly Leu Gln Gly Pro Pro Gly Lys Leu Gly Pro Pro Gly
65                  70                  75                  80

Asn Pro Gly Pro Ser Gly Ser Pro Gly Pro Lys Gly Gln Lys Gly Asp
                85                  90                  95
```

-continued

```
Pro Gly Lys Ser Pro Asp Gly Asp Ser Ser Leu Ala Ala Ser Glu Arg
            100                 105                 110
Lys Ala Leu Gln Thr Glu Met Ala Arg Ile Lys Lys Trp Leu Thr Phe
        115                 120                 125
Ser Leu Gly Lys Gln Val Gly Asn Lys Phe Phe Leu Thr Asn Gly Glu
    130                 135                 140
Ile Met Thr Phe Glu Lys Val Lys Ala Leu Cys Val Lys Phe Gln Ala
145                 150                 155                 160
Ser Val Ala Thr Pro Arg Asn Ala Ala Glu Asn Gly Ala Ile Gln Asn
                165                 170                 175
Leu Ile Lys Glu Glu Ala Phe Leu Gly Ile Thr Asp Glu Lys Thr Glu
            180                 185                 190
Gly Gln Phe Val Asp Leu Thr Gly Asn Arg Leu Thr Tyr Thr Asn Trp
        195                 200                 205
Asn Glu Gly Glu Pro Asn Asn Ala Gly Ser Asp Glu Asp Cys Val Leu
    210                 215                 220
Leu Leu Lys Asn Gly Gln Trp Asn Asp Val Pro Cys Ser Thr Ser His
225                 230                 235                 240
Leu Ala Val Cys Glu Phe Pro Ile
                245
```

<210> SEQ ID NO 3
<211> LENGTH: 1696
<212> TYPE: DNA
<213> ORGANISM: Human

<400> SEQUENCE: 3

```
gcgcgaattc tgctccgtgt ccgacatgct gcgccgcgct ctgctgtgcc tgccgtgggc     60
cgccctggtg cgcgccgacg cccccgagga ggaggaccac gtcttggtgc tgcggaaaag    120
caacttcgcg gaggcgctgg cggcccacaa gtacccgccg tggagttcc  atgcccctg     180
gtgtggccac tgcaaggctc tggcccctga gtatgccaaa gccgctggga agctgaaggc    240
agaaggttcc gagatcaggt tggccaaggt ggacgccacg gaggagtctg acctagccca    300
gcagtacggc gtgcgcggct atcccaccat caagttcttc aggaatggag acacggcttc    360
ccccaaggaa tatacagctg cagagaggc  tgatgacatc gtgaactggc tgaagaagcg    420
cacgggcccg gctgccacca ccctgcctga cggcgcagct gcagagtcct ggtggagtc     480
cagcgaggtg gccgtcatcg gcttcttcaa ggacgtggag tcggactctg ccaagcagtt    540
tttgcaggca gcagaggcca tcgatgacat accatttggg atcacttcca acagtgacgt    600
gttctccaaa taccagctcg acaaagatgg ggttgtcctc tttaagaagt ttgatgaagg    660
ccggaacaac tttgaagggg aggtcaccaa ggagaacctg ctggacttta tcaaacacaa    720
ccagctgccc cttgtcatcg agttcaccga gcagacagcc cgaagatttt tggaggtga    780
atcaagact  cacatcctgc tgttcttgcc caagagtgtg tctgactatg acggcaaact    840
gagcaacttc aaaacagcag ccgagagctt caagggcaag atcctgttca tcttcatcga    900
cagcgaccac accgacaacc agcgcatcct cgagttcttt ggcctgaaga aggaagagtg    960
cccggccgtg cgcctcatca ccttggagga ggagatgacc aagtacaagc ccgaatcgga   1020
ggagctgacg gcagagagga tcacagagtt ctgccaccgc ttcctggagg gcaaaatcaa   1080
gcccacctg  atgagccagg agctgccgga ggactgggac aagcagcctg tcaaggtgct   1140
tgttgggaag aactttgaag acgtggcttt tgatgagaaa aaaacgtctt  tgtggagtt   1200
ctatgcccca tggtgtggtc actgcaaaca gttggctccc atttgggata aactgggaga   1260
```

-continued

```
gacgtacaag gaccatgaga acatcgtcat cgccaagatg gactcgactg ccaacgaggt       1320
ggaggccgtc aaagtgcacg gcttccccac actcgggttc tttcctgcca gtgccgacag       1380
gacggtcatt gattacaacg gggaacgcac gctggatggt tttaagaaat tcctagagag       1440
cggtggccaa gatggggcag gggatgttga cgacctcgag gacctcgaag aagcagagga       1500
gccagacatg gaggaagacg atgaccagaa agctgtgaaa gatgaactgt aatacgcaaa       1560
gccggacccg ggcgctgccg agacccctcg ggggctgcac acccagcagc agcgcacgcc       1620
tccgaagcct gcggcctcgc ttgaaggagg cgtcgccgg  aaacccaagg aacctctctg       1680
aagtgcggcc gcgcgc                                                       1696
```

<210> SEQ ID NO 4
<211> LENGTH: 508
<212> TYPE: PRT
<213> ORGANISM: Human

<400> SEQUENCE: 4

```
Met Leu Arg Arg Ala Leu Leu Cys Leu Ala Val Ala Ala Leu Val Arg
  1               5                  10                  15

Ala Asp Ala Pro Glu Glu Asp His Val Leu Val Leu Arg Lys Ser
             20                  25                  30

Asn Phe Ala Glu Ala Leu Ala Ala His Lys Tyr Pro Pro Val Glu Phe
         35                  40                  45

His Ala Pro Trp Cys Gly His Cys Lys Ala Leu Ala Pro Glu Tyr Ala
     50                  55                  60

Lys Ala Ala Gly Lys Leu Lys Ala Glu Gly Ser Glu Ile Arg Leu Ala
 65                  70                  75                  80

Lys Val Asp Ala Thr Glu Glu Ser Asp Leu Ala Gln Gln Tyr Gly Val
                 85                  90                  95

Arg Gly Tyr Pro Thr Ile Lys Phe Phe Arg Asn Gly Asp Thr Ala Ser
            100                 105                 110

Pro Lys Glu Tyr Thr Ala Gly Arg Glu Ala Asp Asp Ile Val Asn Trp
        115                 120                 125

Leu Lys Lys Arg Thr Gly Pro Ala Ala Thr Thr Leu Pro Asp Gly Ala
130                 135                 140

Ala Ala Glu Ser Leu Val Glu Ser Ser Glu Val Ala Val Ile Gly Phe
145                 150                 155                 160

Phe Lys Asp Val Glu Ser Asp Ser Ala Lys Gln Phe Leu Gln Ala Ala
                165                 170                 175

Glu Ala Ile Asp Asp Ile Pro Phe Gly Ile Thr Ser Asn Ser Asp Val
            180                 185                 190

Phe Ser Lys Tyr Gln Leu Asp Lys Asp Gly Val Val Leu Phe Lys Lys
        195                 200                 205

Phe Asp Glu Gly Arg Asn Asn Phe Glu Gly Glu Val Thr Lys Glu Asn
    210                 215                 220

Leu Leu Asp Phe Ile Lys His Asn Gln Leu Pro Leu Val Ile Glu Phe
225                 230                 235                 240

Thr Glu Gln Thr Ala Pro Lys Ile Phe Gly Gly Glu Ile Lys Thr His
                245                 250                 255

Ile Leu Leu Phe Leu Pro Lys Ser Val Ser Asp Tyr Asp Gly Lys Leu
            260                 265                 270

Ser Asn Phe Lys Thr Ala Ala Glu Ser Phe Lys Gly Lys Ile Leu Phe
        275                 280                 285
```

```
Ile Phe Ile Asp Ser Asp His Thr Asp Asn Gln Arg Ile Leu Glu Phe
    290                 295                 300
Phe Gly Leu Lys Lys Glu Glu Cys Pro Ala Val Arg Leu Ile Thr Leu
305                 310                 315                 320
Glu Glu Glu Met Thr Lys Tyr Lys Pro Glu Ser Glu Leu Thr Ala
                325                 330                 335
Glu Arg Ile Thr Glu Phe Cys His Arg Phe Leu Glu Gly Lys Ile Lys
                340                 345                 350
Pro His Leu Met Ser Gln Glu Leu Pro Glu Asp Trp Asp Lys Gln Pro
                355                 360                 365
Val Lys Val Leu Val Gly Lys Asn Phe Glu Asp Val Ala Phe Asp Glu
    370                 375                 380
Lys Lys Asn Val Phe Val Glu Phe Tyr Ala Pro Trp Cys Gly His Cys
385                 390                 395                 400
Lys Gln Leu Ala Pro Ile Trp Asp Lys Leu Gly Glu Thr Tyr Lys Asp
                405                 410                 415
His Glu Asn Ile Val Ile Ala Lys Met Asp Ser Thr Ala Asn Glu Val
                420                 425                 430
Glu Ala Val Lys Val His Gly Phe Pro Thr Leu Gly Phe Phe Pro Ala
            435                 440                 445
Ser Ala Asp Arg Thr Val Ile Asp Tyr Asn Gly Glu Arg Thr Leu Asp
    450                 455                 460
Gly Phe Lys Lys Phe Leu Glu Ser Gly Gly Gln Asp Gly Ala Gly Asp
465                 470                 475                 480
Val Asp Asp Leu Glu Asp Leu Glu Glu Ala Glu Glu Pro Asp Met Glu
                485                 490                 495
Glu Asp Asp Asp Gln Lys Ala Val Lys Asp Glu Leu
                500                 505

<210> SEQ ID NO 5
<211> LENGTH: 1978
<212> TYPE: DNA
<213> ORGANISM: Human

<400> SEQUENCE: 5
gcgcggatcc agggtaggaa gtagccgctc cgagtggagg cgactggggg ctgaagagcg     60
cgccgccctc tcgtcccact ttccaggtgt gtgatcctgt aaaattaaat cttccaagat    120
gatctggtat atattaatta taggaattct gcttccccag tctttggctc atccaggctt    180
ttttacttca attggtcaga tgactgattt gatccatact gagaaagatc tggtgacttc    240
tctgaaagat tatattaagg cagaagagga caagttagaa caaataaaaa aatgggcaga    300
gaagttagat cggctaacta gtacagcgac aaaagatcca gaaggatttg ttgggcatcc    360
agtaaatgca ttcaaattaa tgaaacgtct gaatactgag tggagtgagt tggagaatct    420
ggtccttaag gatatgtcag atggctttat ctctaaccta accattcaga gaccagtact    480
ttctaatgat gaagatcagg ttggggcagc caaagctctg ttacgtctcc aggatacctag   540 caatttggat acagatacca ctcaaagggt aatcttcca ggagtgaaac acaaatcttt     600
tctaacggct gaggactgct ttgagttggg caaagtggcc tatacagaag cagattatta    660
ccatacggaa ctgtggatgg aacaagccct aaggcaactg atgaaggcg agatttctac     720 catagataaa gtctctgttc tagattattt gagctatgcg gtatatcagc agggagacct    780
ggataaggca cttttgctca caaagaagct tcttgaacta gatcctgaac atcagagagc    840
taatggtaac ttaaaatatt ttgagtatat aatggctaaa gaaaaagatg tcaataagtc    900
```

-continued

```
tgcttcagat gaccaatctg atcagaaaac tacaccaaag aaaaaagggg ttgctgtgga    960
ttacctgcca gagagacaga agtacgaaat gctgtgccgt ggggagggta tcaaaatgac   1020
ccctcggaga cagaaaaaac tcttttgccg ctaccatgat ggaaaccgta atcctaaatt   1080
tattctggct ccagctaaac aggaggatga atgggacaag cctcgtatta ttcgcttcca   1140
tgatattatt tctgatgcag aaattgaaat cgtcaaagac ctagcaaaac caaggctgag   1200
ccgagctaca gtacatgacc ctgagactgg aaaattgacc acagcacagt acagagtatc   1260
taagagtgcc tggctctctg gctatgaaaa tcctgtggtg tctcgaatta atatgagaat   1320
acaagatcta acaggactag atgtttccac agcagaggaa ttacaggtag caaattatgg   1380
agttggagga cagtatgaac cccatttga  ctttgcacgg aaagatgagc cagatgcttt   1440
caaagagctg ggacaggaa  atagaattgc tacatggctg ttttatatga gtgatgtgtc   1500
tgcaggagga gccactgttt tcctgaagt  tggagctagt gtttggccca aaaaaggaac   1560
tgctgttttc tggtataatc tgtttgccag tggagaagga gattatagta cacggcatgc   1620
agcctgtcca gtgctagttg gcaacaaatg ggtatccaat aaatggctcc atgaacgtgg   1680
acaagaattt cgaagacctt gtacgttgtc agaattggaa tgacaaacag gcttcccttt   1740
ttctcctatt gttgtactct tatgtgtctg atatacacat ttccatagtc ttaactttca   1800
ggagtttaca attgactaac actccatgat tgattcagtc atgaacctca tcccatgttt   1860
catctgtgga caattgctta ctttgtgggt tcttttaaaa gtaacacgaa atcatcatat   1920
tgcataaaac cttaaagttc tgttggtatc acagaagaca aggcagagga attcgcgc     1978
```

<210> SEQ ID NO 6
<211> LENGTH: 534
<212> TYPE: PRT
<213> ORGANISM: Human

<400> SEQUENCE: 6

```
Met Ile Trp Tyr Ile Leu Ile Gly Ile Leu Leu Pro Gln Ser Leu
 1               5                  10                  15

Ala His Pro Gly Phe Phe Thr Ser Ile Gly Gln Met Thr Asp Leu Ile
                20                  25                  30

His Thr Glu Lys Asp Leu Val Thr Ser Leu Lys Asp Tyr Ile Lys Ala
            35                  40                  45

Glu Glu Asp Lys Leu Glu Gln Ile Lys Lys Trp Ala Glu Lys Leu Asp
        50                  55                  60

Arg Leu Thr Ser Thr Ala Thr Lys Asp Pro Glu Gly Phe Val Gly His
    65                  70                  75                  80

Pro Val Asn Ala Phe Lys Leu Met Lys Arg Leu Asn Thr Glu Trp Ser
                85                  90                  95

Glu Leu Glu Asn Leu Val Leu Lys Asp Met Ser Asp Gly Phe Ile Ser
            100                 105                 110

Asn Leu Thr Ile Gln Arg Pro Val Leu Ser Asn Asp Glu Asp Gln Val
        115                 120                 125

Gly Ala Ala Lys Ala Leu Leu Arg Leu Gln Asp Thr Tyr Asn Leu Asp
    130                 135                 140

Thr Asp Thr Ile Ser Lys Gly Asn Leu Pro Gly Val Lys His Lys Ser
145                 150                 155                 160

Phe Leu Thr Ala Glu Asp Cys Phe Glu Leu Gly Lys Val Ala Tyr Thr
                165                 170                 175

Glu Ala Asp Tyr Tyr His Thr Glu Leu Trp Met Glu Gln Ala Leu Arg
```

```
                      180                 185                 190
        Gln Leu Asp Glu Gly Glu Ile Ser Thr Ile Asp Lys Val Ser Val Leu
                195                 200                 205
        Asp Tyr Leu Ser Tyr Ala Val Tyr Gln Gln Gly Asp Leu Asp Lys Ala
                210                 215                 220
        Leu Leu Leu Thr Lys Lys Leu Leu Glu Leu Asp Pro Glu His Gln Arg
        225                 230                 235                 240
        Ala Asn Gly Asn Leu Lys Tyr Phe Glu Tyr Ile Met Ala Lys Glu Lys
                        245                 250                 255
        Asp Val Asn Lys Ser Ala Ser Asp Asp Gln Ser Asp Gln Lys Thr Thr
                    260                 265                 270
        Pro Lys Lys Lys Gly Val Ala Val Asp Tyr Leu Pro Glu Arg Gln Lys
                    275                 280                 285
        Tyr Glu Met Leu Cys Arg Gly Glu Gly Ile Lys Met Thr Pro Arg Arg
                290                 295                 300
        Gln Lys Lys Leu Phe Cys Arg Tyr His Asp Gly Asn Arg Asn Pro Lys
        305                 310                 315                 320
        Phe Ile Leu Ala Pro Ala Lys Gln Glu Asp Glu Trp Asp Lys Pro Arg
                        325                 330                 335
        Ile Ile Arg Phe His Asp Ile Ile Ser Asp Ala Glu Ile Glu Ile Val
                    340                 345                 350
        Lys Asp Leu Ala Lys Pro Arg Leu Ser Arg Ala Thr Val His Asp Pro
                    355                 360                 365
        Glu Thr Gly Lys Leu Thr Thr Ala Gln Tyr Arg Val Ser Lys Ser Ala
                370                 375                 380
        Trp Leu Ser Gly Tyr Glu Asn Pro Val Val Ser Arg Ile Asn Met Arg
        385                 390                 395                 400
        Ile Gln Asp Leu Thr Gly Leu Asp Val Ser Thr Ala Glu Glu Leu Gln
                        405                 410                 415
        Val Ala Asn Tyr Gly Val Gly Gly Gln Tyr Glu Pro His Phe Asp Phe
                    420                 425                 430
        Ala Arg Lys Asp Glu Pro Asp Ala Phe Lys Glu Leu Gly Thr Gly Asn
                    435                 440                 445
        Arg Ile Ala Thr Trp Leu Phe Tyr Met Ser Asp Val Ser Ala Gly Gly
                450                 455                 460
        Ala Thr Val Phe Pro Glu Val Gly Ala Ser Val Trp Pro Lys Lys Gly
        465                 470                 475                 480
        Thr Ala Val Phe Trp Tyr Asn Leu Phe Ala Ser Gly Glu Gly Asp Tyr
                        485                 490                 495
        Ser Thr Arg His Ala Ala Cys Pro Val Leu Val Gly Asn Lys Trp Val
                    500                 505                 510
        Ser Asn Lys Trp Leu His Glu Arg Gly Gln Glu Phe Arg Arg Pro Cys
                    515                 520                 525
        Thr Leu Ser Glu Leu Glu
            530

<210> SEQ ID NO 7
<211> LENGTH: 1292
<212> TYPE: DNA
<213> ORGANISM: Human

<400> SEQUENCE: 7
ggtaccatgc gctccctcct gcttctcagc gccttctgcc tcctggaggc ggccctggcc      60
gccgaggtga agaaacctgc agccgcagca gctcctggca ctgcggagaa gttgagcccc     120
```

-continued

```
aaggcggcca cgcttgccga gcgcagcgcc ggcctggcct tcagcttgta ccaggccatg      180
gccaaggacc aggcagtgga gaacatcctg gtgtcacccg tggtggtggc ctcgtcgctg      240
gggctcgtgt cgctgggcgg caaggcgacc acggcgtcgc aggccaaggc agtgctgagc      300
gccgagcagc tgcgcgacga ggaggtgcac gccggcctgg gcgagctgct gcgctcactc      360
agcaactcca cggcgcgcaa cgtgacctgg aagctgggca gccgactgta cggacccagc      420
tcagtgagct cgctgatgac ttcgtgcgc agcagcaagc agcactacaa ctgcgagcac      480
tccaagatca acttccgcga caagcgcagg ccgctgcagt ccatcaacga gtgggccgcg      540
cagaccaccg acggcaagct gcccgaggtc accaaggacg tggagcgcac ggacggcgcc      600
ctgttagtca cgccatgtt cttcaagcca cactgggatg agaaattcca ccacaagatg      660
gtggacaacc gtggcttcat ggtgactcgg tcctataccg tgggtgtcat gatgatgcac      720
cggacaggcc tctacaacta ctacgacgac gagaaggaaa agctgcaaat cgtggagatg      780
cccctggccc acaagctctc cagcctcatc atcctcatgc cccatcacgt ggagcctctc      840
gagcgccttg aaaagctgct aaccaaagag cagctgaaga tctggatggg gaagatgcag      900
aagaaggctg ttgccatctc cttgcccaag ggtgtggtgg aggtgaccca tgacctgcag      960
aaacacctgg ctgggctggg cctgactgag gccattgaca gaacaaggc cgacttgtca     1020 cgcatgtcag gcaagaagga cctgtacctg ccagcgtgt ccacgccac cgcctttgag     1080 ttggacacag atggcaaccc ctttgaccag gacatctacg ggcgcgagga gctgcgcagc     1140
cccaagctgt tctacgccga ccacccttc atcttcctag tgcgggacac ccaaagcggc     1200
tccctgctat tcattgggcg cctggtccgg cctaagggtg acaagatgcg agacgagtta     1260
tagggcctca gggtgcacac aggatggcag ga                                   1292
```

<210> SEQ ID NO 8
<211> LENGTH: 418
<212> TYPE: PRT
<213> ORGANISM: Human

<400> SEQUENCE: 8

```
Met Arg Ser Leu Leu Leu Ser Ala Phe Cys Leu Leu Glu Ala Ala
  1               5                  10                  15

Leu Ala Ala Glu Val Lys Lys Pro Ala Ala Ala Ala Pro Gly Thr
                 20                  25                  30

Ala Glu Lys Leu Ser Pro Lys Ala Ala Thr Leu Ala Glu Arg Ser Ala
             35                  40                  45

Gly Leu Ala Phe Ser Leu Tyr Gln Ala Met Ala Lys Asp Gln Ala Val
         50                  55                  60

Glu Asn Ile Leu Val Ser Pro Val Val Ala Ser Ser Leu Gly Leu
 65                  70                  75                  80

Val Ser Leu Gly Gly Lys Ala Thr Thr Ala Ser Gln Ala Lys Ala Val
                 85                  90                  95

Leu Ser Ala Glu Gln Leu Arg Asp Glu Val His Ala Gly Leu Gly
             100                 105                 110

Glu Leu Leu Arg Ser Leu Ser Asn Ser Thr Ala Arg Asn Val Thr Trp
         115                 120                 125

Lys Leu Gly Ser Arg Leu Tyr Gly Pro Ser Val Ser Phe Ala Asp
     130                 135                 140

Asp Phe Val Arg Ser Lys Gln His Tyr Asn Cys Glu His Ser Lys
145                 150                 155                 160
```

```
Ile Asn Phe Arg Asp Lys Arg Arg Pro Leu Gln Ser Ile Asn Glu Trp
                165                 170                 175

Ala Ala Gln Thr Thr Asp Gly Lys Leu Pro Glu Val Thr Lys Asp Val
            180                 185                 190

Glu Arg Thr Asp Gly Ala Leu Leu Val Asn Ala Met Phe Phe Lys Pro
        195                 200                 205

His Trp Asp Glu Lys Phe His His Lys Met Val Asp Asn Arg Gly Phe
    210                 215                 220

Met Val Thr Arg Ser Tyr Thr Val Gly Val Met Met His Arg Thr
225                 230                 235                 240

Gly Leu Tyr Asn Tyr Tyr Asp Asp Glu Lys Glu Lys Leu Gln Leu Val
                245                 250                 255

Glu Met Pro Leu Ala His Lys Leu Ser Ser Leu Ile Ile Leu Met Pro
            260                 265                 270

His His Val Glu Pro Leu Glu Arg Leu Glu Lys Leu Leu Thr Lys Glu
        275                 280                 285

Gln Leu Lys Ile Trp Met Gly Lys Met Gln Lys Lys Ala Val Ala Ile
    290                 295                 300

Ser Leu Pro Lys Gly Val Val Glu Val Thr His Asp Leu Gln Lys His
305                 310                 315                 320

Leu Ala Gly Leu Gly Leu Thr Glu Ala Ile Asp Lys Asn Lys Ala Asp
                325                 330                 335

Leu Ser Arg Met Ser Gly Lys Lys Asp Leu Tyr Leu Ala Ser Val Phe
            340                 345                 350

His Ala Thr Ala Phe Glu Leu Asp Thr Asp Gly Asn Pro Phe Asp Gln
        355                 360                 365

Asp Ile Tyr Gly Arg Glu Glu Leu Arg Ser Pro Lys Leu Phe Tyr Ala
    370                 375                 380

Asp His Pro Phe Ile Phe Leu Val Arg Asp Thr Gln Ser Gly Ser Leu
385                 390                 395                 400

Leu Phe Ile Gly Arg Leu Val Arg Pro Lys Gly Asp Lys Met Arg Asp
                405                 410                 415

Glu Leu

<210> SEQ ID NO 9
<211> LENGTH: 34
<212> TYPE: DNA
<213> ORGANISM: Human

<400> SEQUENCE: 9
gcgcgaattc accatggccc tgtttccatc actc                              34

<210> SEQ ID NO 10
<211> LENGTH: 30
<212> TYPE: DNA
<213> ORGANISM: Human

<400> SEQUENCE: 10
caagggcggc cgcagtgata tgacccttca                                  30

<210> SEQ ID NO 11
<211> LENGTH: 7
<212> TYPE: DNA
<213> ORGANISM: Human
<220> FEATURE:
<221> NAME/KEY: misc_structure
<222> LOCATION: (2)..(3)
<223> OTHER INFORMATION: n at positions 2 and 3 is a or g or c or t.
```

```
<400> SEQUENCE: 11 annatgg                                                                7

<210> SEQ ID NO 12
<211> LENGTH: 40
<212> TYPE: DNA
<213> ORGANISM: Human

<400> SEQUENCE: 12
gcttcccagg caaagatggg cgtgatggca ccaagggaga                            40

<210> SEQ ID NO 13
<211> LENGTH: 40
<212> TYPE: DNA
<213> ORGANISM: Human

<400> SEQUENCE: 13
cttggcctgg ttccccpttt tctcccttgg tgccatcacg                            40

<210> SEQ ID NO 14
<211> LENGTH: 34
<212> TYPE: DNA
<213> ORGANISM: Human

<400> SEQUENCE: 14
gcgcctcgag aaaagagaaa ctgtgacctg tgag                                  34

<210> SEQ ID NO 15
<211> LENGTH: 30
<212> TYPE: DNA
<213> ORGANISM: Human

<400> SEQUENCE: 15
gcgcgaattc tgctccgtgt ccgacatgct                                       30

<210> SEQ ID NO 16
<211> LENGTH: 32
<212> TYPE: DNA
<213> ORGANISM: Human

<400> SEQUENCE: 16
gcgcgcggcc gcacttcaga gaggttcctt gg                                    32

<210> SEQ ID NO 17
<211> LENGTH: 35
<212> TYPE: DNA
<213> ORGANISM: Human

<400> SEQUENCE: 17
ctcgagaaga gagacgcccc cgaggaggag gacca                                 35

<210> SEQ ID NO 18
<211> LENGTH: 27
<212> TYPE: DNA
<213> ORGANISM: Human

<400> SEQUENCE: 18
ggtaccttac agttcatctt tcacagc                                          27

<210> SEQ ID NO 19
<211> LENGTH: 30
<212> TYPE: DNA
```

```
<213> ORGANISM: Human

<400> SEQUENCE: 19
gcgcggatcc agggtaggaa gtagccgctc                                    30

<210> SEQ ID NO 20
<211> LENGTH: 30
<212> TYPE: DNA
<213> ORGANISM: Human

<400> SEQUENCE: 20
gcgcgaattc ctctgccttg tcttctgtga                                    30

<210> SEQ ID NO 21
<211> LENGTH: 46
<212> TYPE: DNA
<213> ORGANISM: Human

<400> SEQUENCE: 21
ggtaccatgc gctccctcct gcttctcagc gccttctgcc tcctgg                  46

<210> SEQ ID NO 22
<211> LENGTH: 25
<212> TYPE: DNA
<213> ORGANISM: Human

<400> SEQUENCE: 22
tcctgccatc ctgtgtgcac cctga                                         25

<210> SEQ ID NO 23
<211> LENGTH: 7
<212> TYPE: DNA
<213> ORGANISM: Human
<220> FEATURE:
<221> NAME/KEY: misc_structure
<222> LOCATION: (2)..(3)
<223> OTHER INFORMATION: n at positions 2 and 3 is a or g or c or t.

<400> SEQUENCE: 23 annatgg                                                             7

<210> SEQ ID NO 24
<211> LENGTH: 1558
<212> TYPE: DNA
<213> ORGANISM: RAT

<400> SEQUENCE: 24
ggaccaagaa gtccccactt tgattgtggt ctgcttcagc aaattcttgt cacaaaacag   60
agactttgac ctgaccagat cttgggagca tagtcacaac tcagagtagg tgaggcctca  120
aaatgtaaag gtggcatttt tacttgaaat atgaaccact gctggctgag aaacagatct  180
cctgagtcct tagcttcccc ctctacaatc tgggttgagg acccatgggg aaagggaaaa  240
gtggggaact gcgatttctg tgaaatagaa ggggagccaa gaaacagagg tccagggtcc  300
tttgggtgct aggcagtcta catccctgcc agaccaccac aagcgtggct ggtttatact  360
tctcagggtt gtaaggcctc aggtcacac aatctaaccc ttaaacatgg tgtccacagg  420
gatgctggac ctcccttcct cttgcatctt tcttggtttt agccctgacc tgactcccgt  480
ttctacatca gtagcctcgg ctgtgaccca ccttgagtag tagttcagaa ccagagggta  540
tgatatcccc cacatctgct cctcccggct ggggtgcag actgctaggg ctaagaacaa  600
aagctttaag gccaagtgtg aggtggaatt cgtctcatta actttctccc ccctcaggga  660
```

-continued

```
agggaccatg ctcctgcttc cactgctcgt ccttctctgt gtagtgagcg tgtcctcatc      720
agggtcacaa acctgtgagg aaaccctgaa gacttgctct gtgatagcct gcggcagaga      780
cgggagagat gggcccaaag gggagaaggg agaaccaggt atggaacccc gtattctggc      840
tttctacact tttacctccg taggcgactg ttctgaattc agagatgatg cgcagggacc      900
tggggaggct tggctttcat cgtgtcatgt tcttcccctc ataacaatct ctcagcagta      960
tcactgcctc ccagtcaaca gtgcttaaca gctctctcga gtctcataca gggtctgtga     1020
ggtggggctg tccctcagga cagatattcc gacttgactc accaatacct agctctcagg     1080
ctctttcttg gagtcagtgt ggatcaaact ttgaacttct agagaaaaag agtgagtaac     1140
agccaccgga acatgctgcc tttatctccc gacaggtcaa gggctcaggg gcttgcaggg     1200
ccctccaggg aaactggggc ctccaggaag tgtaggagcc cctggaagtc aaggaccaaa     1260
aggccaaaaa gggatcgtg gagacagcag aggtaagaga ctgccttacc atgactagct      1320
tgagtggggg ttgtgtccta ggaaaaagaa gccatgagcc tctggtcttt atggctcatc     1380
aggacatgct catgtttctt gactcagtgt cacgatgtct gcaagaaata ccctccaggg     1440
ccattccccc accagttctc tttaggacac cgggttagct tttcttcagg tggaagtcca     1500
gtgtgtaatc caggctatga gggaggactg tgccctcctc catgtcttct gaaagtggg      1558

<210> SEQ ID NO 25
<211> LENGTH: 1211
<212> TYPE: DNA
<213> ORGANISM: Mouse

<400> SEQUENCE: 25
tagagtcccc ccacccatct tttggtagga acagaggcaa tttggagtta gattatttat       60
tcaatttcac agagctcagt ggtagaacca gtttataagc ttcatcgagt ctgactccag      120
gatgccagtt ctgtagggtc agatcttgct cactaaaata gaatgtgggc tactttgtaa      180
tccttggatc tagaccagac gatggaacca atcatgtttc ttctagctgt ggccagatag      240
acccagccat ttttgtctga ttgagagtta acagaatggt agaattcaca gttccagata      300
acctgtgctc cacactgcag atctcaacat acaaagatat gcctgtttat tcgtatttaa      360
aagaaaaaag taagataaca attaaactag agctttgggt aaaaagaagt gtgttctgat      420
ttgttgtaag catctcacaa tgggtctcaa gaatgaagac acccattatg ttttacgcta      480
ccagagaaga tagagtatac atggctccat ttgaacttca cacaatgagt gctctagaag      540
ataagtcggt atcacccacc ttttttatat tttaggggtg ctcttctctc tgagtgaaaa      600
agttggaaag aagtattttg tgagcagtgt taaaagatg agccttgata gagtgaaggc       660
cctgtgctcc gaattccagg gctctgtggc cactccagg aatgctgagg aaaactcggc       720
catccagaaa gtgccaaag atattgccta cttgggcatc acagatgtga gggttgaagg       780
cagttttgag gatctgacag gaaacagagt gcgctatact aattggaatg atggggagcc      840
caacaacacg ggcgatgggg aagactgtgt ggtgatcttg ggaaatggca gtggaacga      900 tgtcccctgc tctgactctt ttttggcaat atgtgaattc tctgactgag ggtgcttgtt      960
tctcagccct ccttgattct ttagggtact cctgacgtcc gcagtttgtt ctgaaaaata     1020
aaatatggga aaatataaac aattcaacat tggttaccca atgcattctc ttgtgaaggt     1080
gtagaaataa agtgagttta gttttcattt atgactcttg tgctctgtgg ggtcctcttt     1140
tcttcttggt aatggcgttt ccctgtgtat ttgagtttct tagcccagtc tcaggtatta     1200
```

```
aaagggtcta c                                                         1211

<210> SEQ ID NO 26
<211> LENGTH: 714
<212> TYPE: DNA
<213> ORGANISM: CHICKEN

<400> SEQUENCE: 26
atgatggcaa caagtttact taccacagat aaacctgaag agaaaatgta ttcctgtccc      60
atcattcagt gtagtgctcc tgcagtcaat ggattaccag gcagagatgg aagagatggt     120
cccaaagggg aaaagggaga cccaggagaa ggactgagag gtctgcaggg tttgcctgga     180
aaagcaggac cccaaggatt aaaaggagag gtgggaccac aaggagagaa aggtcaaaaa     240
ggagaacgtg gaattgttgt aactgatgac ctgcaccgac aaataactga tttggaagca     300
aaaatccggg tattggaaga tgacttaagc agatacaaaa aagccttgag tttaaaggac     360
gtcgtaaaca ttggtaaaaa aatgtttgtc tcaactggaa agaaatataa ttttgaaaag     420
ggaaaatccc tttgtgcaaa agctggaagt gtgcttgcct ctcctaggaa cgaggctgag     480
aatacagctt taaaagactt aattgaccct tcaagccaag cttatattgg gatatctgat     540
gcacaaactg agggcagatt catgtacctg agtggtgggc ctttaactta cagcaactgg     600
aaacctggag aaccaaataa tcacaaaaat gaagactgtg cggtgataga agactctgga     660
aaatggaatg atttagactg ttcaaattca aatatcttca ttatttgtga attg          714
```